(12) United States Patent
Ananda et al.

(10) Patent No.: US 10,403,395 B2
(45) Date of Patent: Sep. 3, 2019

(54) METHOD AND APPARATUS FOR GENERATING OBJECTIVE MEDICAL SECOND OPINION

(71) Applicant: SecondOpinionExpert, Inc., Westlake Village, CA (US)

(72) Inventors: Mohan Ananda, Westlake Village, CA (US); Andre Henderson, North Hollywood, CA (US)

(73) Assignee: SecondOpinionExpert, Inc., Westlake Village, CA (US)

( * ) Notice: Subject to any disclaimer, the term of this patent is extended or adjusted under 35 U.S.C. 154(b) by 239 days.

(21) Appl. No.: 14/053,464

(22) Filed: Oct. 14, 2013

(65) Prior Publication Data
US 2015/0106117 A1   Apr. 16, 2015

(51) Int. Cl.
  *G06F 19/00* (2018.01)
  *G16H 15/00* (2018.01)
  *G16H 50/20* (2018.01)

(52) U.S. Cl.
  CPC ............. *G16H 15/00* (2018.01); *G16H 50/20* (2018.01)

(58) Field of Classification Search
  CPC .. G06F 19/3418; G06F 19/324; G06F 19/325; G06F 19/321; G06F 16/51; G06F 16/5866; G06F 19/3456; G06F 19/3481; G06F 16/24578; G06Q 50/24; G16H 50/20; G16H 50/50; G16H 10/60; G16H 15/00
  See application file for complete search history.

(56) References Cited

U.S. PATENT DOCUMENTS

| | | | | |
|---|---|---|---|---|
| 2002/0035486 A1* | 3/2002 | Huyn | | G06F 19/363 705/3 |
| 2003/0140063 A1* | 7/2003 | Pizzorno | | G06F 19/345 |
| 2009/0276242 A1* | 11/2009 | Waisbren | | G06Q 10/10 705/2 |
| 2011/0313258 A1* | 12/2011 | Chopra | | G06F 19/363 600/300 |
| 2012/0035944 A1 | 2/2012 | Gobel | | |

(Continued)

OTHER PUBLICATIONS

World Intellectual Property Organization, International Search Report and Written Opinion for International Application No. PCT/US2014/059616, dated Jan. 22, 2015, pp. 1-12.

*Primary Examiner* — Maroun P Kanaan
(74) *Attorney, Agent, or Firm* — Law Offices of M. Kala Sarvaiya; M. Kala Sarvaiya

(57) ABSTRACT

A system is disclosed to provide a user the ability to obtain an objective medical second opinion generated by the system and approved by a licensed physician on the web through the Internet. The system enables the user to upload all available medical records. The system generates a current user medical status report in a comprehensive form with proper hyperlinks to the appropriate medical records including diagnostic images and results of other diagnostic procedures up loaded to the system in a digital or in a paper form such that the current status report is available to a consultant physician with all the proper hyperlinked attachments for review. The system generates a suggested second opinion consultant report by processing an evidence based diagnosis method incorporated into the system by utilizing all the data relevant to the user that is available to the system.

16 Claims, 16 Drawing Sheets

(56) References Cited

U.S. PATENT DOCUMENTS

2013/0060576 A1\* 3/2013 Hamm ................ G06F 19/3418
705/2
2013/0173287 A1 7/2013 Cashman et al.
2013/0226601 A1\* 8/2013 Razmi ................ G06F 19/3418
705/2

\* cited by examiner

METHOD AND APPARATUS FOR GENERATING OBJECTIVE MEDICAL SECOND OPINION

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

1. Field

This disclosure relates to the field of using technology for improving healthcare and in particular using a web based platform to provide a medical second opinion to a user. The system described herein uses a software architecture that ensures secure data communications for receiving and analyzing data related to a patient's medical condition and the system then generates a second medical opinion using evidence based diagnosis methods.

2. Description of the Related Art

A patient suffering from a medical concern visits a physician to evaluate his medical issue. The patient usually receives an opinion from the physician as to the cause of the patient's medical concern. The physician usually provides advice as to how to treat the patient's medical concern. In some instances, the physician may refer the patient to a specialist or may request the patient to undergo diagnostic tests to evaluate the patient's medical concern.

In many instances, patients desire a second medical opinion regarding the patient's medical concern and treatment options. In some cases, insurance carriers require patients to obtain a second opinion. Patients may seek a second medical opinion to determine if less invasive procedures may exist to treat the medical concern. Similarly, patients may seek a second medical opinion to determine if other treatment options exist for the patient.

Computer-based systems exist to allow patients and physicians to store patient information. Systems also exist that allow patients to upload medical files to allow a physician to view information relating to the patient. In addition, systems exist for digitizing imaging data. Systems also exist for determining a patient's medical history. However, systems do not exist that generate an extensive report about a patient's medical history and thereafter generate a second opinion based on the system's elaborate and extensive analysis and reporting capabilities.

The advent of the Affordable Care Act (ACA) will inject about 30 million more individuals into the healthcare system. This may create difficulties and delays for more individuals seeking timely, expert medical advice and consultations.

Patients will have even more difficulty receiving medical second opinions from physicians. A medical second opinion is a valuable resource when a patient is faced with difficult health circumstances or choices regarding the treatment options.

This is especially difficult due to limited access to highly specialized care depending on where one lives and their availability for travel or mobility.

In some instances, a patient's insurance company may require a medical second opinion. In fact, Medicare generally encourages patients to obtain second, and even third, medical opinions.

Medical second opinions are important for patients as it gives patients options as to how to handle their concern. For example, by obtaining a medical second opinion, a patient may find out that he does not need a certain treatment or procedure. Or, the patient may learn that he has a less expensive option, thereby saving the patient a large medical bill.

Further, some patients may wish to obtain a medical second opinion to alleviate their concerns about the risk or how it might affect their lifestyle, family or work. Therefore, there exists a need to improve access to care and to allow patients to seek and obtain objective medical second opinions.

Throughout this description, elements appearing in figures are assigned three-digit or four-digit reference designators, where the most significant digit is the figure number and the two least significant digits are specific to the element. An element that is not described in conjunction with a figure may be presumed to have the same characteristics and function as a previously-described element having a reference designator with the same least significant digits.

DETAILED DESCRIPTION

Description of Apparatus

For purposes of this patent, the term "patient" as used herein means an individual who has a complaint relating to a potential or actual medical condition. The patient may also be an individual who receives medical attention, care, or treatment. For purposes of this patent, the term "physician" means a person licensed to practice medicine.

Described herein is a system for generating an objective second opinion for a patient. One of the primary objectives of the system is to leverage technology to assist a qualified physician in any specialty to analyze all of the medical data pertaining to a patient and be able to use his experience and judgment to achieve an unbiased second opinion regarding the conditions of the patient. The unbiased second opinion may assist the physician in making a better treatment plan to address the patient's medical concerns. The system for generating an objective second medical opinion is used by a patient who has already visited and obtained a medical opinion from a physician regarding a medical concern. The physician may have performed diagnostic tests on the patient relating to the medical concern. Following the physician's analysis, the physician may have provided the patient the results of any medical exams performed and the physician's opinion as to how to treat the patient's medical concern.

The patient, having already received a first opinion from a physician, may desire an objective second opinion. An objective second opinion is an unbiased opinion generated by the system based on data and information received from a patient and based on the medical information in the system. The patient may use the system shown in FIG. 1 to receive an objective second opinion.

Figure 1:
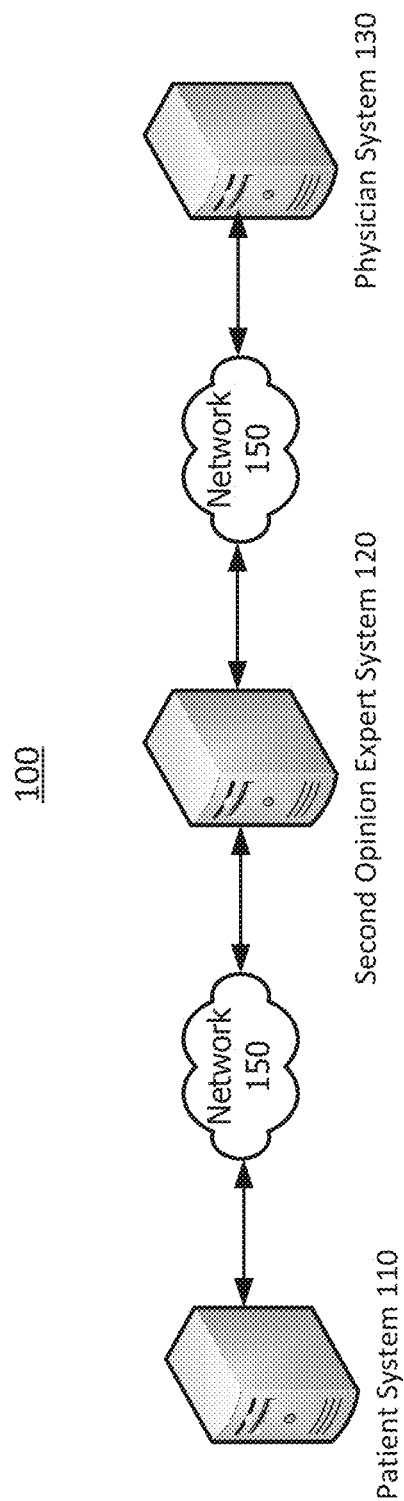
FIG. 1 is a block diagram of an environment for a system for generating an objective second medical opinion.

Referring now to FIG. 1, there is shown an environment 100 for a system for generating an objective second medical opinion. The environment 100 includes patient system 110, second opinion expert system 120 and physician system 130, all of which are interconnected via network 150. The network 150 may be a Local Area Network (LAN), a Wide Area Network (WAN), a Storage Area Network (SAN), wired, wireless, or a combination of these, and may include or be the Internet.

An objective medical second opinion expert report is a report containing a medical opinion that is generated by a second opinion expert system, such as second opinion expert system 120 in FIG. 1, and is provided to a patient. The objective medical second opinion expert report is a customized report that generates a second opinion based on a patient's personal information, the patient's medical history, the patient's medical concerns, the patient's medical test results and additional medical information.

The patient system 110 is connected to the network 150. The patient system 110 is a computing device including software suitable for obtaining medical diagnostic data relating to a patient's medical condition. The patient system is associated with a patient (not shown) and is capable of interfacing with the patient to obtain personal information, medical information, historical information and diagnostic information relating to medical exams performed on a patient. The patient system 110 may be a stand-alone computing device, a personal computer, lap-top computer, mobile device, a tablet PC, a personal digital assistant, a smartphone, a server computer operating as a part of a distributed or peer-to-peer network or many other forms, a notebook, a netbook or a mobile phone, that is running software suitable for interfacing with a patient.

Similarly, the second opinion expert (SOE) system 120 is connected to the network 150. The second opinion expert system 120 is a computing device including software suitable for obtaining medical diagnostic data relating to a patient's medical condition, storing medical information and generating second opinion expert reports for a patient. The second opinion expert system 120 may be a stand-alone computing device, a personal computer, lap-top computer, mobile device, a tablet PC, a personal digital assistant, a smartphone, a server computer operating as a part of a distributed or peer-to-peer network or many other forms, a notebook, a netbook or a mobile phone.

Finally, the physician system 130 is connected to the network 150. The physician system 130 is a computing device including software suitable for obtaining medical diagnostic data relating to a patient's medical condition, revising objective second opinion expert reports and transmitting objective second opinion expert reports to the second opinion expert system 120. The physician system is associated with a physician (not shown) and is capable of interfacing with a physician to review and revise second opinion expert reports. The physician system 130 may be a stand-alone computing device, a personal computer, lap-top computer, mobile device, a tablet PC, a personal digital assistant, a smartphone, a server computer operating as a part of a distributed or peer-to-peer network or many other forms, a notebook, a netbook or a mobile phone, that is running software suitable for interfacing with a physician.

The network 150 may take the form of a local network, a wide area network, the Internet or any number of other networks. The network 150 may be implemented locally by physically connected computers or may be distributed over a wide area.

Figure 2:
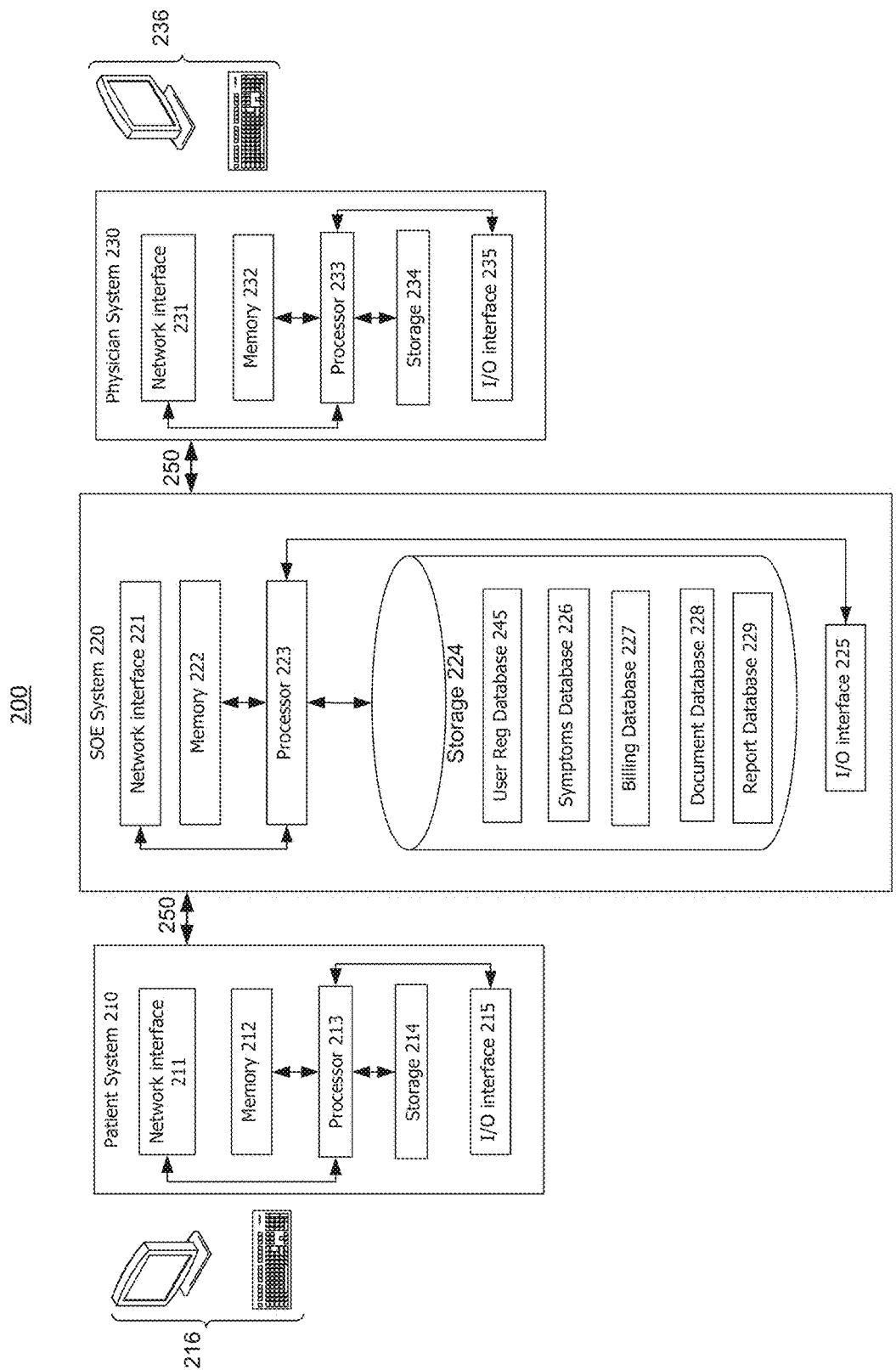
FIG. 2 is a block diagram of a system for generating an objective second medical opinion.

Turning now to FIG. 2, there is shown a block diagram of a system 200 for generating an objective second medical opinion. As in FIG. 1, the system comprises patient system 210, SOE system 220 and physician system 230 all interconnected by the network 250.

The patient system 210 comprises a network interface 211, a memory 212, a processor 213, a storage 214 and an I/O interface 215. The processor 213 may be or include one or more microprocessors, application specific integrated circuits (ASICs), programmable logic devices (PLDs) and programmable logic arrays (PLAs).

The network interface 211 includes an interface to a network such as network 250 and network 150 in FIG. 1.

The memory 212 may be or include RAM, ROM, DRAM, SRAM and MRAM, and may include firmware, such as static data or fixed instructions, BIOS, system functions, configuration data, and other routines used during the operation of the patient system 210 and processor 213. The memory 212 also provides a storage area for data and instructions associated with applications and data handled by the processor 213.

The I/O interface 215 interfaces the processor 213 to peripherals such as display and keyboard 216. The I/O interface also interfaces the processor 213 to peripherals (not shown) such as webcams, fax machines, printers, USB devices, microphones and speakers.

The storage 214 provides non-volatile, bulk or long term storage of data or instructions in the patient system 210. The storage 214 may take the form of a disk, tape, CD, DVD, or other reasonably high capacity addressable or serial storage medium. Multiple storage devices may be provided or available to the patient system 210. Some of these storage devices may be external to the patient system 210, such as network storage or cloud-based storage. As described herein, "storage" does not include transitory medium such as signals or electrical current. "Storage" as used herein is limited to non-transitory storage medium.

The SOE system 220 comprises a network interface 221, a memory 222, a processor 223, and a storage 224. The processor 223 is similar to processor 213 and it may be or include one or more microprocessors, application specific integrated circuits (ASICs), programmable logic devices (PLDs) and programmable logic arrays (PLAs).

The network interface 221 includes an interface to a network such as network 250 and network 150 in FIG. 1. The network interface 221 is similar to network interface 211 in patient system 210.

The memory 222 is similar to memory 212 in patient system 210. The memory 222 212 may be or include RAM, ROM, DRAM, SRAM and MRAM, and may include firmware, such as static data or fixed instructions, BIOS, system functions, configuration data, and other routines used during the operation of the SOE system 220 and processor 223. The memory 222 also provides a storage area for data and instructions associated with applications and data handled by the processor 223.

The I/O interface 225 interfaces with the processor 223 to peripherals, such as displays, keyboards, webcams, fax machines, printers, USB devices, microphones and speakers (not shown).

The storage 224 provides non-volatile, bulk or long term storage of data or instructions in the SOE system 220. The storage 224 may take the form of a disk, tape, CD, DVD, or other reasonably high capacity addressable or serial storage medium. Multiple storage devices may be provided or available to the SOE system 220. Some of these storage devices may be external to the SOE system 220, such as network storage or cloud-based storage. In this patent, the term "storage medium" does not encompass transient media such as signals and waveforms that convey, but do not store information.

The storage 224 may store data required for the system. For example, the storage may have a user registration database 245, a symptoms database 226, a billing database 227, a document database 228 and a report database 229. The user registration database 245 may include information regarding a user's account information, his login information, and security questions that may be asked in the event the user requests a new password for his account. The symptoms database 226 may include information regarding medical conditions and symptoms related to those medical conditions. For example, the symptoms database may include an entry for the common cold having symptoms such as stuffy nose, sore throat and chest congestion. The symptom database 226 may organize these using codes unique to particular symptoms or medical conditions. The billing database 227 may include information regarding the user's medical insurance information and payment plan.

The document database 228 is a database that may store documents relating to the patient's medical history or relating to the patient's first medical opinion. The document database may store links to locations on the system where the documents are actually stored. The document database 228 may also include a Dicom (Digital Imaging and Communications) database. A Dicom database is a database that stores digital images relating medical diagnostic test results. The Dicom standard is a standard for transferring images and associated information between devices. It provides a standard for how digital diagnostic images are to be transferred. The Dicom database stores the digital images in a manner that is compliant with the Dicom standard.

The report database 229 may store reports that are generated by the system for the patient. For example, the system may store a current status report which is generated by the system. In addition, the system may store a suggested second opinion report and a final report, all of which are generated by the system. The report database 229 may also store the transcription and recording of video conferences that are held between a physician and a user.

It is to be understood that the databases shown in the storage 224, can be merged into one database or can exist in separate databases. The databases as shown in FIG. 2 is merely exemplary and it is not required that the system have this storage organization. Additional databases may also be used to store the data required by the system.

The physician system 230 comprises a network interface 231, a memory 232, a processor 233, a storage 234 and an I/O interface 235. The processor 233 may be or include one or more microprocessors, application specific integrated circuits (ASICs), programmable logic devices (PLDs) and programmable logic arrays (PLAs).

The network interface 231 includes an interface to a network such as network 250 and network 150 in FIG. 1.

The memory 232 may be or include RAM, ROM, DRAM, SRAM and MRAM, and may include firmware, such as static data or fixed instructions, BIOS, system functions, configuration data, and other routines used during the operation of the patient system 210 and processor 213. The memory 232 also provides a storage area for data and instructions associated with applications and data handled by the processor 213.

The I/O interface 235 interfaces the processor 233 to peripherals such as display and keyboard 236. The I/O interface 235 also interfaces the processor 233 to peripherals (not shown) such as webcams, fax machines, printers, USB devices, microphones and speakers.

The storage 234 provides non-volatile, bulk or long term storage of data or instructions in the physician system 230. The storage 234 may take the form of a disk, tape, CD, DVD, or other reasonably high capacity addressable or serial storage medium. Multiple storage devices may be provided or available to the physician system 230. Some of these storage devices may be external to the physician system 230, such as network storage or cloud-based storage. In this patent, the term "storage medium" does not encompass transient media such as signals and waveforms that convey, but do not store information.

The patient system 210 and the physician system 230 may also comprise a display and an input unit such as 216 and 236. The SOE system may also comprise a display and an input unit, although not shown in the figure. Further, the patient system 210 and the physician system 230 may also comprise additional components such as a webcam for having video conferences on the system, printers, fax machines, scanners, microphones, speakers and USB devices.

The system can connect patients with the diagnostic expertise of experienced, renowned physicians who will review the patient's individual situation with the specific symptoms, test results and images and provide a comprehensive report which the patient can share and discuss with the family and the primary care physician. The system is a web-based HIPAA compliant and secure system that allows patients a convenient way to register and upload their medical information, test results and diagnostic images. The system is designed to ensure compliance with the HIPAA encryption standards to ensure the security and privacy of an individual's Protected Health Information (PHI). The system will be updated to support new standards issued by the National Institute of Standards and Technology (NIST) regarding the HIPAA encryption standards.

The system may be integrated with various medical insurance carriers such that a patient's bill may be sent to the appropriate carrier. The system may also handle disbursements to physicians and patient payment processing options.

The system may follow up with patients about three to six months after the patient uses the system to determine how the patient is doing. The system may use the follow up information from the patient to update the patient's information in the system.

Some of the benefits of the second opinion expert system include a review and validation of the original diagnoses and opinions and treatment plans and, if necessary, feedback to the patient on alternate and more appropriate plans of treatment. In addition, the availability of these services through a panel of independent, renowned, world-class physicians with substantial experience at leading medical centers without any need for the patient to travel.

Description of Processes

Figure 3:
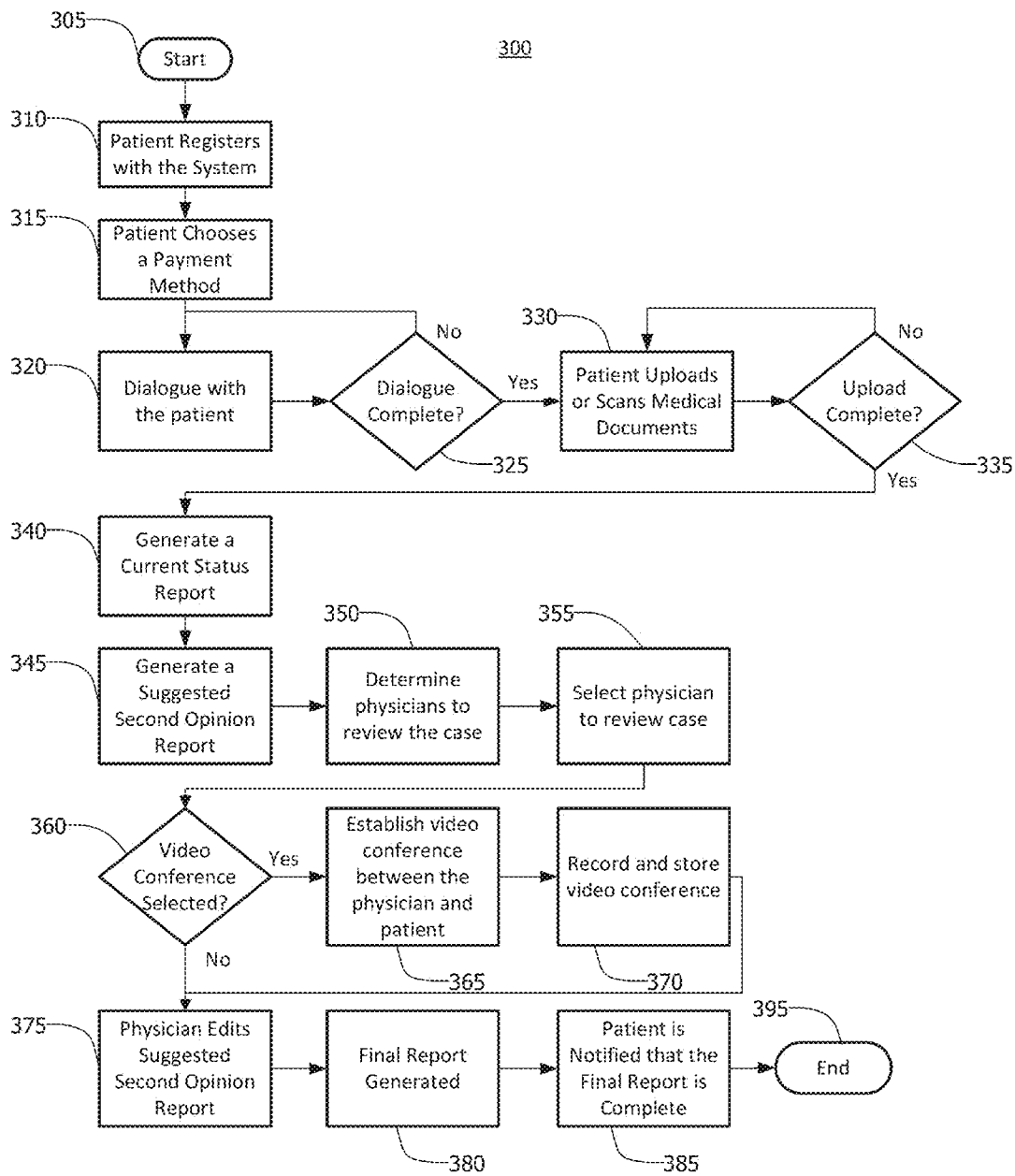
FIG. 3 is a flowchart for generating a second medical opinion.

Referring now to FIG. 3, a process 300 for generating an objective second opinion is shown. The process 300 may start at 305 and may finish at 395. The process may be started by a patient using a patient system, such as patient system 110 in FIG. 1.

The process 300 may begin with a user registering with the system at 310. A user registers with the system by entering personal information, such as his name, birth date and gender. After entering personal information, the user may choose a username and password that is secure and unique to the user. After selecting a username and password, the user may login into the system and start a second opinion expert report case.

As a part of the registration process, the user may select to have a video consultation (described below with reference to elements 360-370) with a physician after the second opinion expert report is generated. If the user selects a video consultation with a physician, then the user and the physician will have a video conference to discuss the second opinion expert report after the report is generated. During the video conference, the user may review the report with the physician and ask the physician any questions or concerns he may have regarding the second opinion recommendation in the report the user received.

After selecting whether the user wants to have a video conference, the user chooses a payment method at 315. At this step, the user enters his medical insurance information into the system so that the system can bill the appropriate insurance on behalf of the patient. In addition, the user may enter a credit card, or bank account information, to keep on file in the event there are expenses that are not covered by the insurance that need to be paid by the user. Alternatively, the system may require the user to pay for the service upfront and then bill the insurance. In such an instance, if the insurance pays the bill, either in full or in part, the user will be credited the amount that the insurance paid. The system may require additional information from the user, such as his contact information, so as to verify whether he is the account holder of the credit card or bank account information that was entered in the system. The system may store the user's medical insurance information as well as any credit card or bank account information in a database so that it will remain on file in the user's account.

Figure 5:
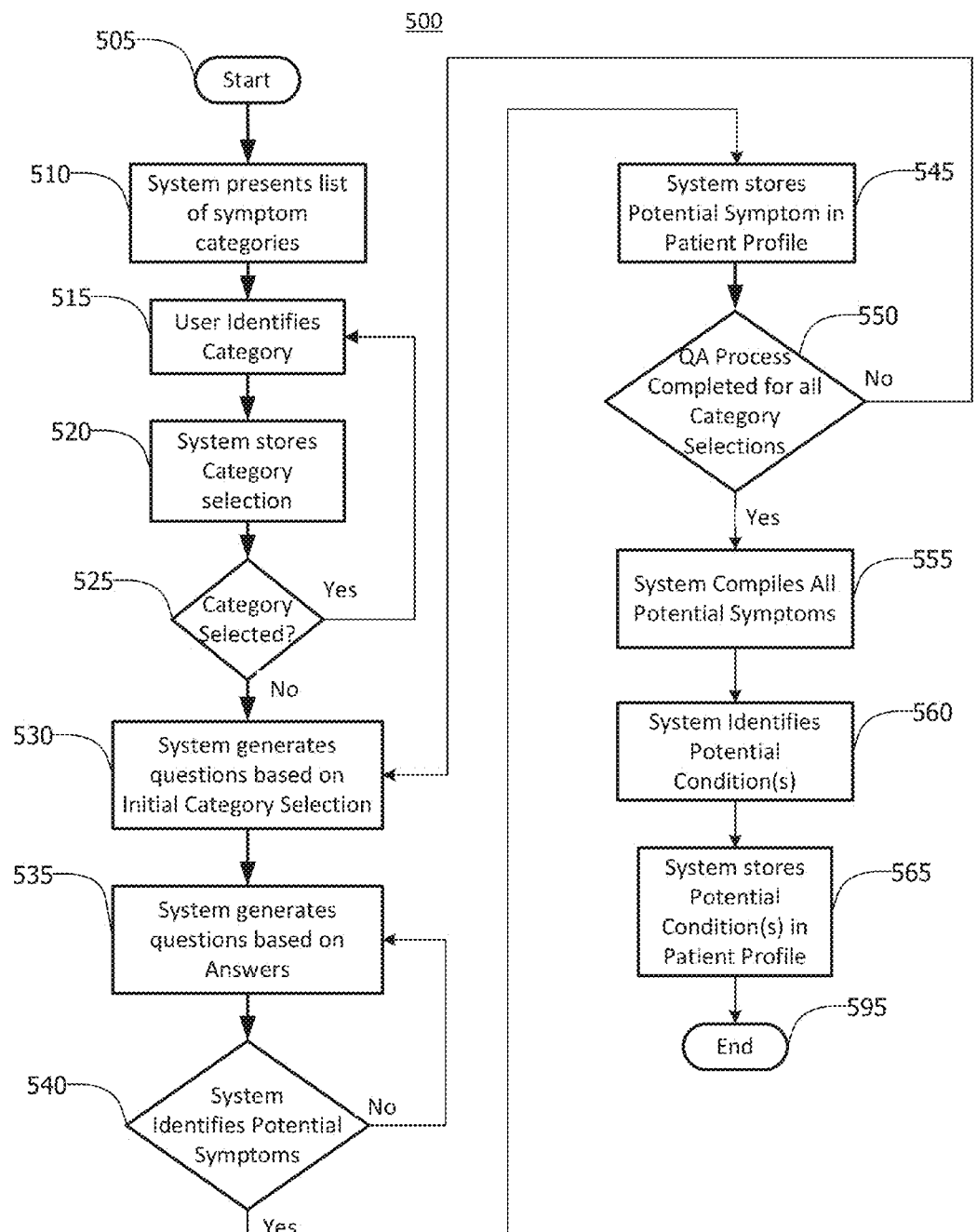
FIG. 5 is a flowchart of a dialogue with the user to generate a second medical opinion.

After the user has entered the payment information at 315, the system starts a dialogue with the user at 320. The system may begin by presenting the user with a set of categories. The categories help the system narrow the user's medical concern. Once the user has selected a category, the system will start generating questions to analyze the user's medical concern. The system continues to generate questions until the system has exhausted all of its analysis. As the patient answers questions from the system, the system generates questions based on the patient's responses and based on similar data stored in the system regarding similar medical conditions of other patients. FIG. 5 provides greater detail as to the dialogue between the user and the system.

Figure 7:
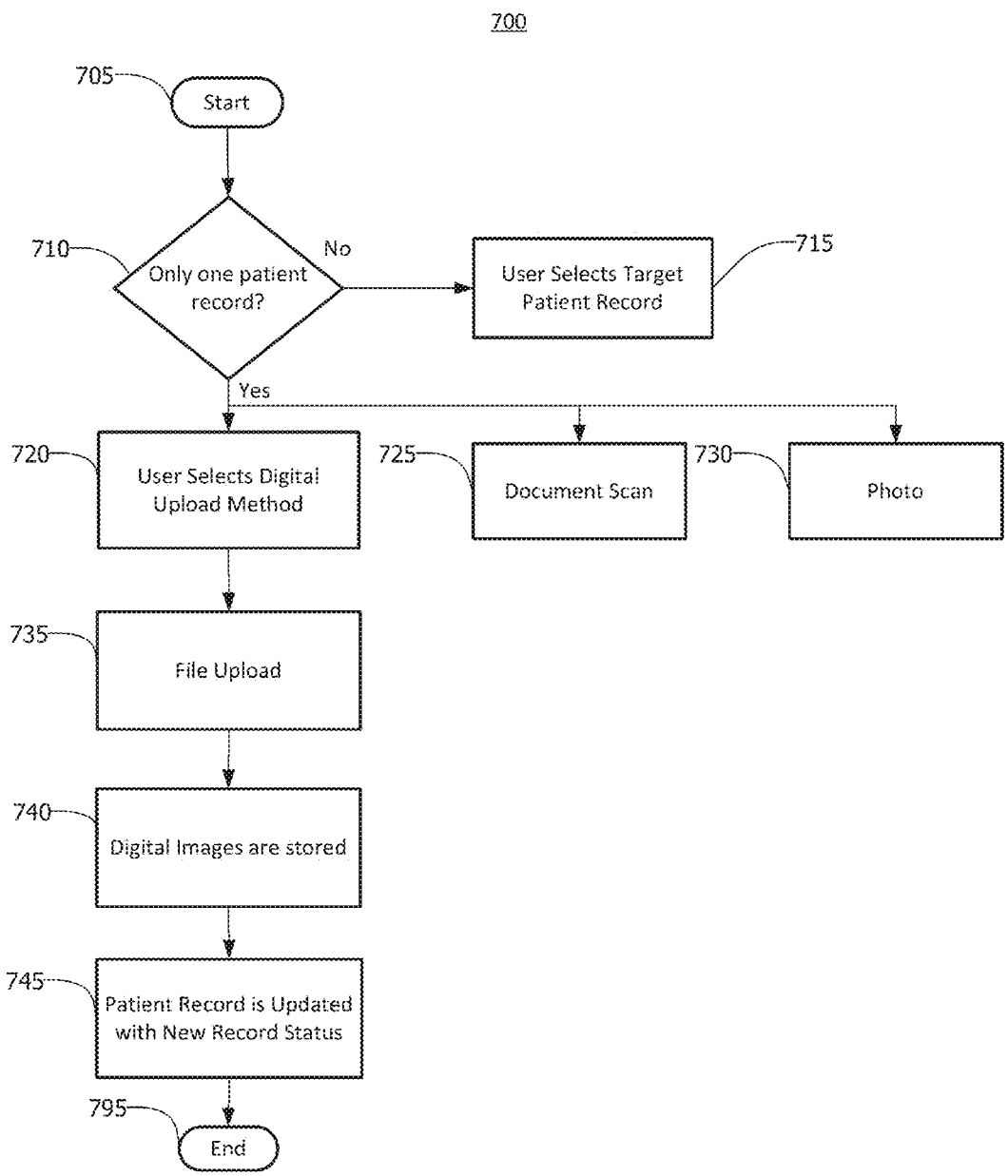
FIG. 7 is a flowchart for uploading digital medical records to be used to generate a second medical opinion.
Figure 8:
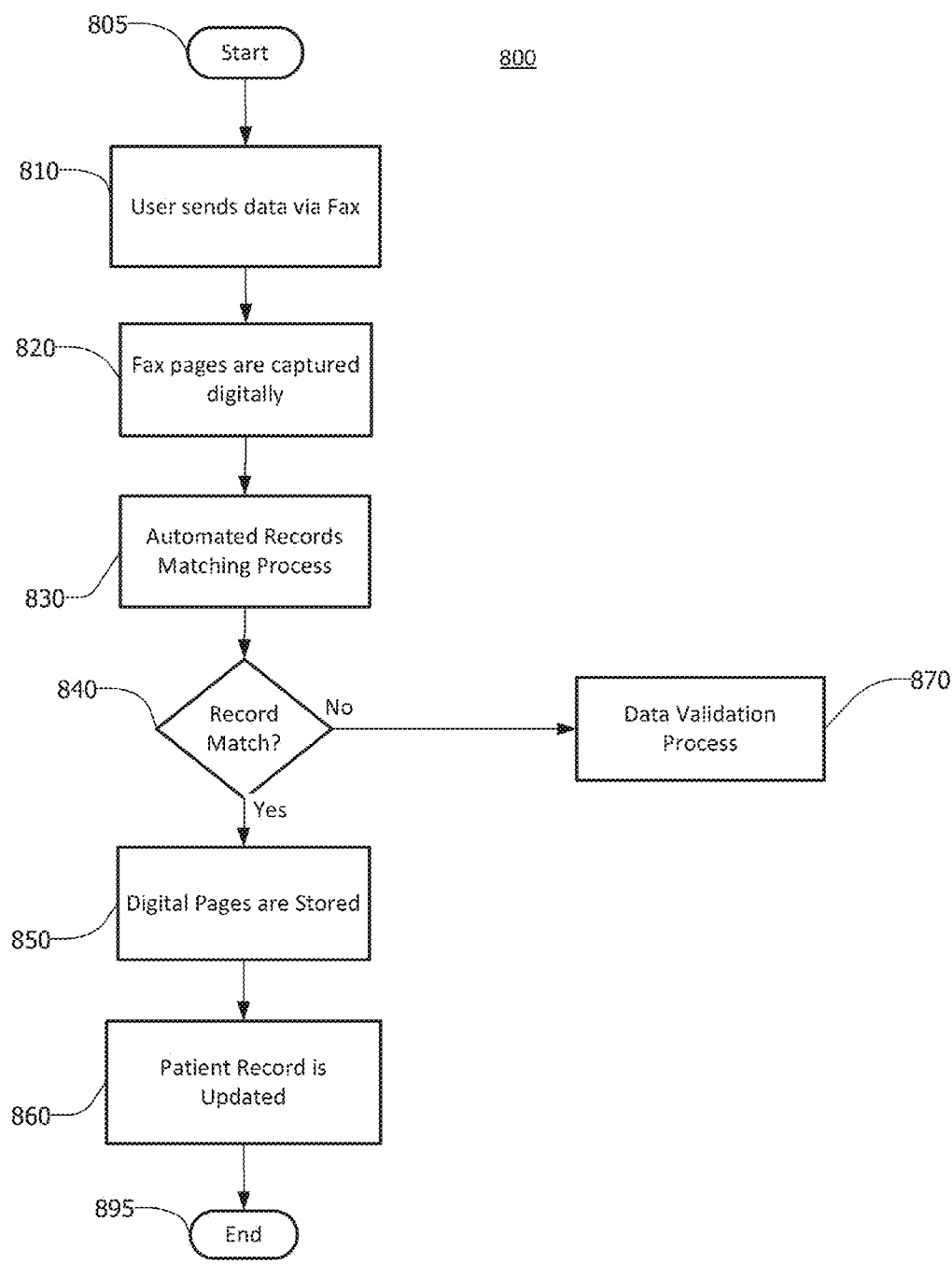
FIG. 8 is a flowchart for faxing medical records to be used to generate a second medical opinion.
Figure 9:
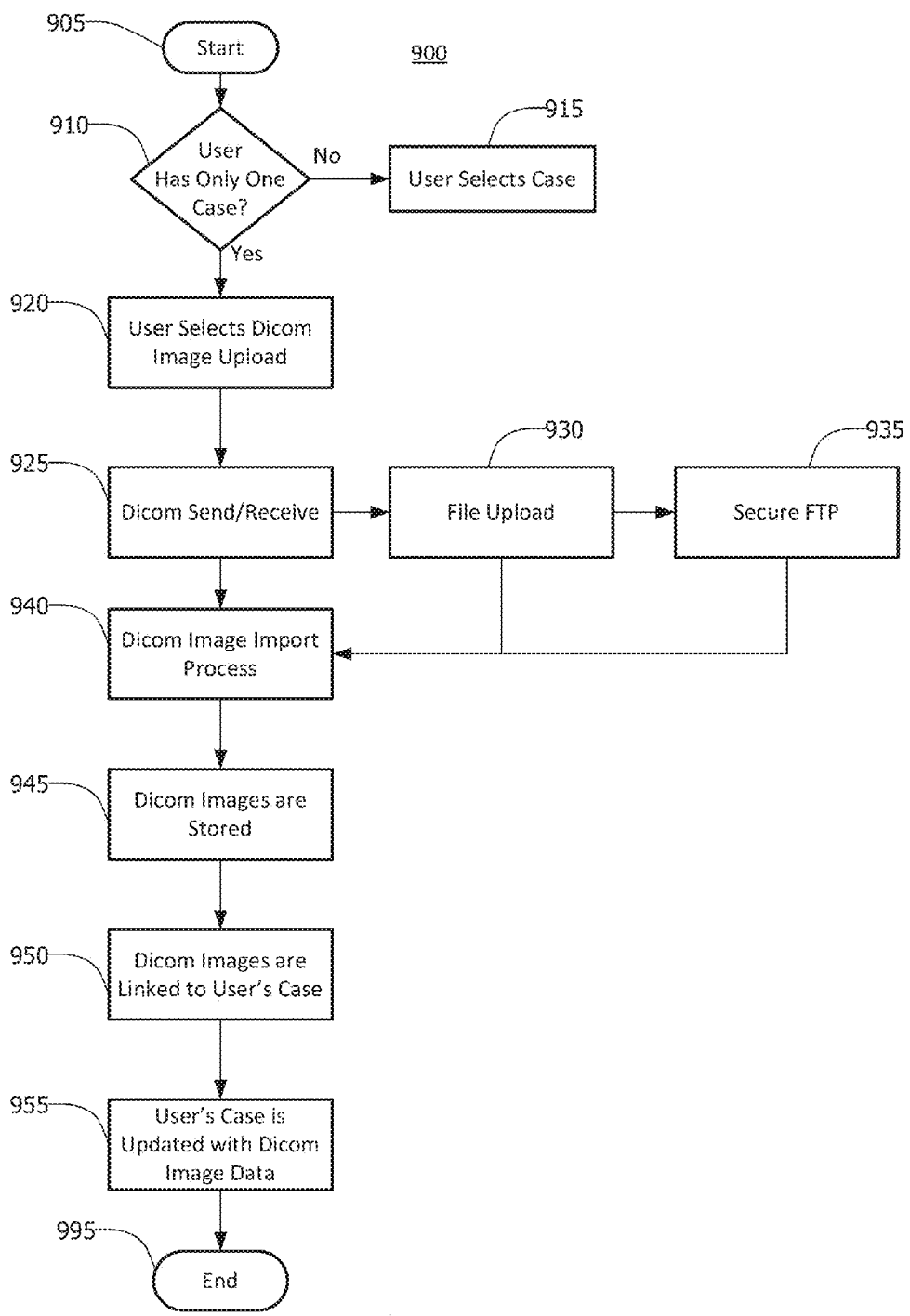
FIG. 9 is a flowchart for uploading Dicom images to be used to generate a second medical opinion.

After the dialogue is complete at 325, the process proceeds to step 330 where the user may upload medical documents that he has received from his physician. For example, the user may have digital or paper documents relating to the user's physician's medical evaluation report. In addition, the user may have diagnostic labs, imaging tests, or other tests that may have been performed by his previous physician. If the user has digital copies of these documents, the user can upload the documents to the system. If the user does not have a digital copy of the document, the user can scan or fax the document electronically and the system will store the documents in the user's account. FIGS. 7, 8 and 9 discuss in greater detail the process for a user to upload or transmit a document to the system. In addition to the methods for uploading documents disclosed in FIGS. 7, 8, and 9, the system is also capable of receiving documents through any additional format for uploading or receiving data. The system is designed to easily adopt new techniques for uploading documents to the system.

Figure 6:
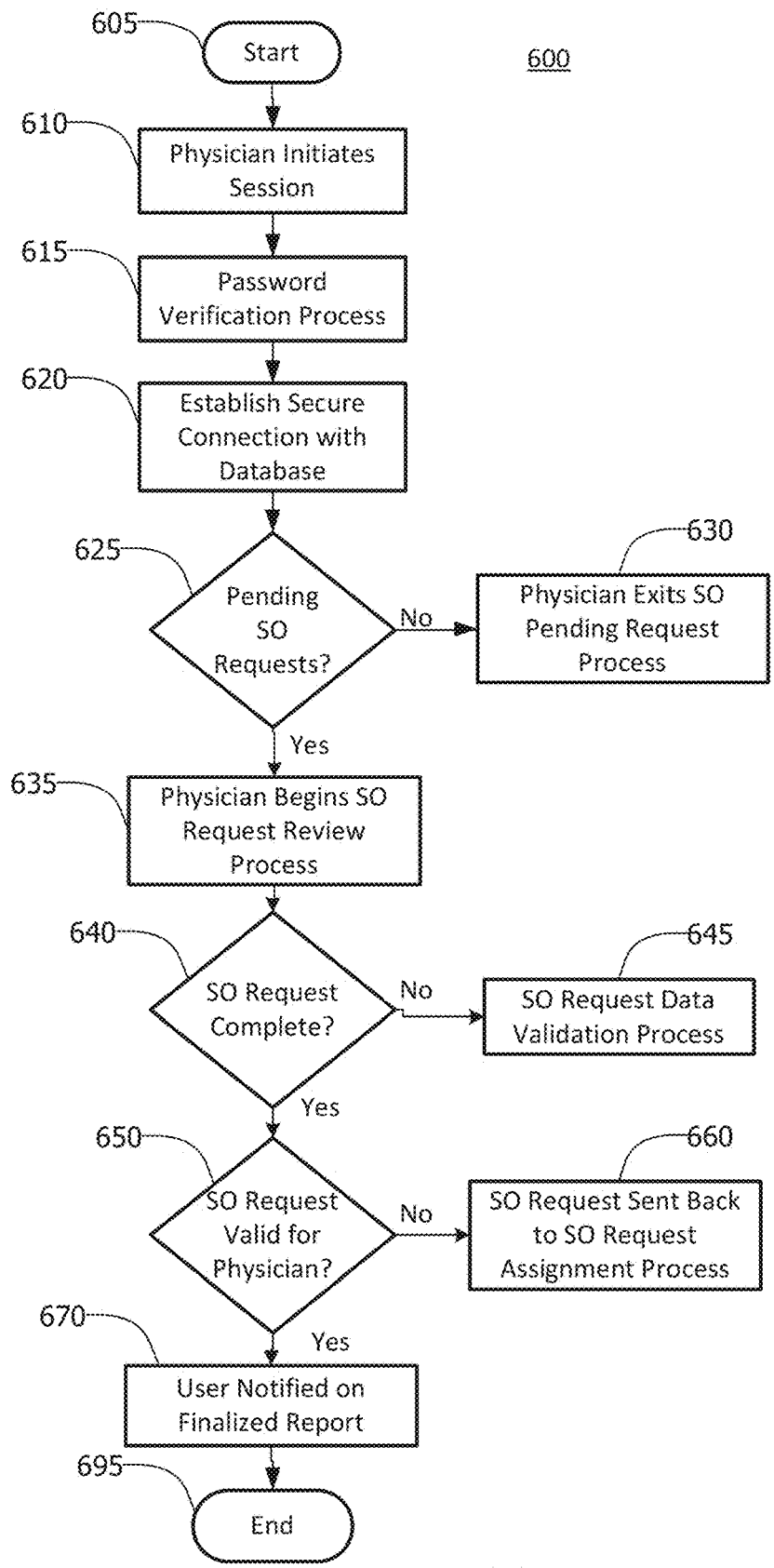
FIG. 6 is a flowchart for the generation of a second medical opinion.

Any document that is uploaded, or transmitted electronically to the system, will remain confidential and the system will not reveal it to anyone other than the patient and the doctors necessary for the second opinion. The documents may be encrypted or may be automatically deleted after the second opinion process is complete. The only individual that may have access to the user's medical data is the physician reviewing the second opinion report generated by the system. FIG. 6 discuss in greater detail the process of a physician logging into the system to review a second opinion report generated by the system.

After the system has questioned the user regarding his medical concern at 320, and after the system has collected all of the user's medical documents at 330, the system proceeds to step 340 where the system generates a current status report. The current status report includes all of the information about the user that was obtained from the dialogue between the user and the system. The current status report also includes secure hyperlinks in the report which link the report to all of the medical documents that were uploaded or transmitted electronically to the system. The secure hyperlinks allow anyone reviewing the report to conveniently access the user's additional medical documents. The current status report is provided to the consulting physician giving the consulting physician a comprehensive status of the patient's current medical condition that includes information regarding the treatment plan suggested by the first physician and also includes hyperlinks to all of the medical data that was uploaded to the system. The current status report allows the consulting physician to obtain a thorough analysis of the patient's condition, thereby allowing the consulting physician to make a well-informed assessment as to the patient's condition. The system is also capable of modifying the presentation of the report. For example, the system may highlight certain portions of the current status report to help the consulting physician assess the patient's condition. The system may store and archive the current status report. The current status report may be used by the system to assess similar medical conditions for other uses of the system.

Figure 11:
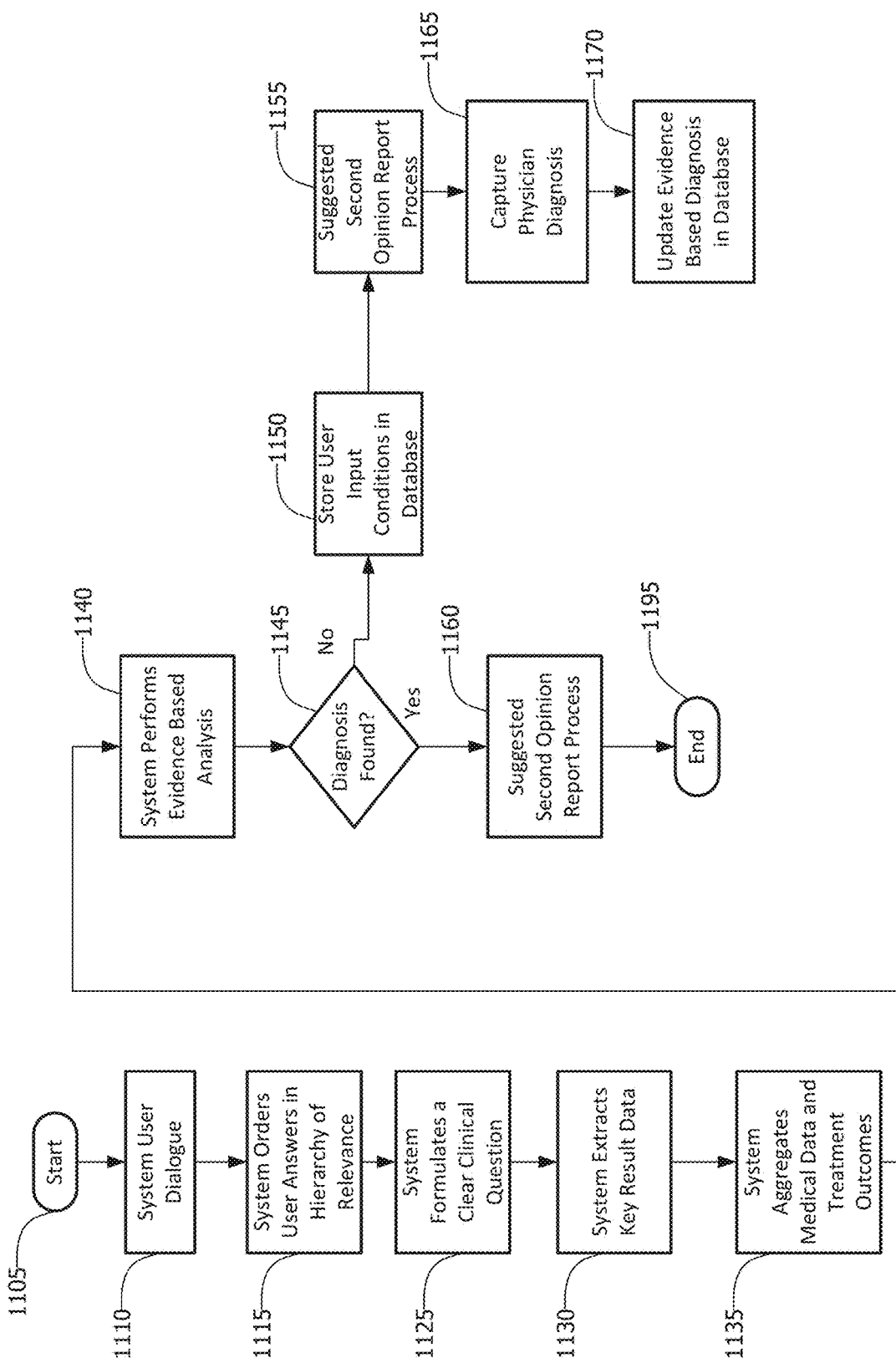
FIG. 11 is a flowchart of an evidence based differential diagnosis to be used to generate a second medical opinion.
Figure 12:
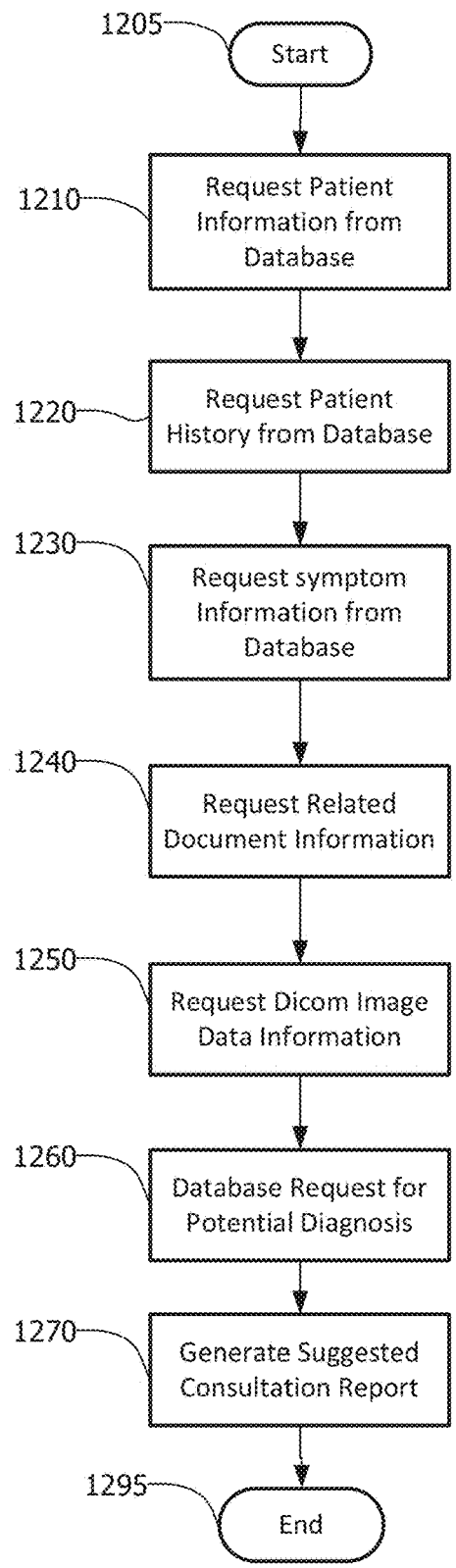
FIG. 12 is a flowchart for generating a suggested second opinion report.

After the system has generated a current status report, the process proceeds to step 345 where the system generates a suggested second opinion report. The suggested second opinion report has a similar format as the current status report in that it also includes all of the user's information regarding his medical concern. The suggested second opinion report also includes secure hyperlinks to the user's medical documents that were uploaded or transmitted to the system. The suggested second opinion report differs from the current status report in that it uses an evidence based differential diagnosis to provide a recommendation for the user as to addressing his medical concern. For example, the system may determine that additional medical tests need to be performed to diagnose a particular condition and the suggested second opinion report would identify the reports that should be performed to complete the diagnosis. Similarly, if the patient's first physician recommended an invasive procedure, the system will evaluate the patient's responses and medical documents and determine if the invasive procedure is essential. In addition, the system will determine if alternate noninvasive or less invasive procedures are available for the patient. If there is an alternate noninvasive or less invasive procedure, the suggested second opinion report will highlight those options for the consulting physician to evaluate when assessing the patient's condition and treatment plan. The suggested second opinion report may be stored and archived in the system. The suggested second report may be used by the system to assess similar medical conditions for other uses of the system. FIG. 11 discusses the evidence based differential diagnosis method in greater detail. FIG. 12 discusses the process of generating a suggested second opinion report in greater detail.

After the system has generated a suggested second opinion expert report at 345, the system proceeds to step 350 where the system determines an appropriate medical specialty and selects all of the possible physicians that specialize in the chosen medical specialty. The system may limit the list of physicians based on the user's state of residence or based on the physician's licensing credentials, or based upon a physician's stated or verified area of expertise.

The system then may send an alert to the physicians who specialize in a selected area and who may live close to the user. The alert may inform the physician that a second opinion report is available. The physicians are generally required to respond within 24 hours of receiving an alert. Otherwise, the system will alert still other physicians in order to move the process forward.

The process proceeds to step 355 after selecting a physician to handle the case.

Here, the system selects the physician who first responds to the alert that the report is ready.

The process then proceeds to step 360 to determine whether the user desires a video conference with the physician. If the user has selected to have a video conference, then the system sends another alert to the physician to schedule a thirty minute session with the user.

After the video conference has been scheduled, the process proceeds to step 365 during which a video conference is activated between the user and the physician. Both the user and the physician have to log in into the system to ensure that the proper individuals are accessing the report. The video conference is thirty minutes, but may voluntarily be extended by agreement of the parties. This extension may require the payment of an additional fee by the patient.

The physician has access to the current status report that was generated by the system and the suggested second opinion report. These reports allow the physician access to the hyperlinked medical documents that were uploaded or transmitted to the system. The video conference allows the physician an opportunity to obtain additional information from the user to help the physician make a proper determination of the patient's condition. The system records and stores the video conference at 370. The system also transcribes the session and stores the digital recording of the video session in a database. The digital recording may be stored in a database in the second opinion expert system, such as second opinion expert system 220 in FIG. 2.

After the consulting physician has concluded the video conference, the physician may edit the suggested second medical opinion report based on his discussion with the user at 375. If the physician did not have a video conference, then he may still edit the suggested second medical opinion report based on his analysis of the patient data and the medical reports.

The consulting physician can then edit the system generated second opinion report to generate a final report at 380. He or she may electronically sign off on the report. The system is designed so that the consulting physician can easily edit and finalize the report using his medical experience and judgment.

At 385, they system notifies the patient that the final second opinion report is ready and the patient can login to the system to obtain a copy of the report. Alternatively, the report may be provided via email to the patient.

The final second opinion report may be stored and archived in the system. The final second report may be used by the system to assess similar medical conditions for other uses of the system.

Figure 4:
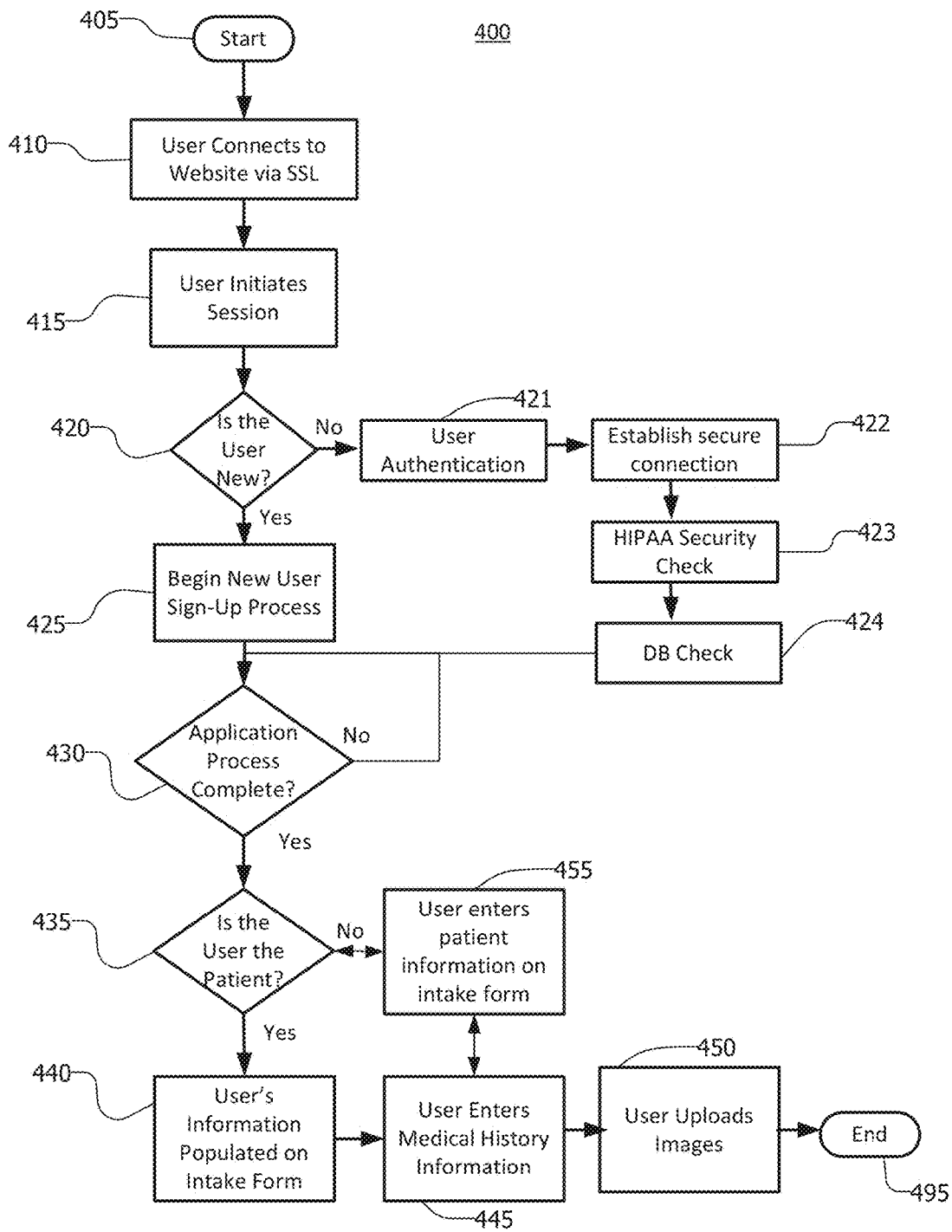
FIG. 4 is a flowchart for the initiation of a generation of a second medical opinion from a patient's perspective.

Referring now to FIG. 4, a process 400 for initiating the generation of a second medical opinion is shown. The process 400 may start at 405 and may finish at 495. The process may be started by a patient using a patient system, such as patient system 110 in FIG. 1.

The process 400 may begin with a user accessing the Internet over a secure network connection, such as Secure Sockets Layer (SSL) or Secure HTTP (S-HTTP). At 405, the user connects to the Internet using the patient system. The connection needs to be a secure connection as personal information may be exchanged during the process. For example, the user's age, gender, city of residence, credit card information and bank account information may be used to complete the user's login to the system.

At 415, the user initiates a session with the system. The user may initiate the system by opening a Web browser. At 415, the user may initiate the session by entering the URL for logging into a web server located on the second opinion expert system, such as SOE 220 in FIG. 2. After the user arrives at the URL, he will have the option of registering as a new user on the website, or logging into the website with an account that has already been registered on the website.

At 420, the SOE system determines whether the user is a new user of the SOE system. If so, then the process proceeds to 425, where the user begins the new user process. A user registers with the system by entering personal information, such as his name, birth date and gender. After entering personal information, the user may choose a username and password that is secure and unique to the user. After selecting a username and password, the user may login into the system and start a second opinion expert report case. The new user process includes identifying a username and password for the user's account. The username is unique for each user.

If at 420, the user is not a new user, then the user is asked to enter the login information for his account. At 421, the system authenticates the user's login information and determines whether the correct username and password information have been entered into the system.

If the user has entered the correct information at 420, then at 422, a secured connection is established between the patient system, such as patient system 110 in FIG. 1, and the SOE system, such as SOE system 120 in FIG. 1. The connection must be secured because sensitive information, such as personal and medical information, is being exchanged. The data exchanged over the connection must be encrypted. The secure connection can be either SSL or S-HTTP.

After a secure connection is established, the process proceeds to 423 where a Health Insurance Portability and Accountability Act (HIPAA) security check is performed which is compliant with the HIPAA Security Rule. HIPAA was developed to protect the privacy and security of health information. The HIPAA Security Rule establishes a national set of security standards for protecting certain health information that is held or transferred in electronic form. The Security Rule requires entities to implement safeguards to ensure that electronic health information will remain secure. The Security Rule protects all identifiable health information that an entity creates, receives, maintains or transmits in electronic form. Therefore at 423, the system confirms that the connection is secure such that any health information that is created in electronic form will remain secure and compliant with the HIPAA Security Rule.

After the HIPAA security check is performed, the process verifies the user's information in the database at 424. In this step, the user registration database, such as user registration database 245 in FIG. 2, may be checked to verify the user's identity and login information.

After the user has logged in, either as an existing user or as a new user, the process proceeds to 430 where it is determined whether the user has completed all of the application information. For example, at 430, the user may need to enter information, such as the user's age and the user's gender. If the user has not completed all of the application information, the process returns back to 430 and continues until the user has entered all of the information required to complete the application for creating a new account.

At 435, the user is asked whether the user is the patient. If the user is the patient, then the process proceeds to step 440 where the user populates an intake form with information relating to himself. The system may ask the user questions regarding the user's current medical concern. In addition, the system may ask if the patient is taking any medications, including prescription and non-prescription medications. Specifically, the system may ask if the patient is taking prescription medicine, or over the counter medicine. The system may ask if the patient is taking any illegal drugs and if so, the names of those drugs. The system may also ask if the patient has any allergies.

If the user is not the patient, then the process proceeds to 455 during which the user will document the patient's information on the intake form.

After the system has completed preparing the intake form, the process proceeds to 445 in which the user enters medical history information. This information may include pre-existing conditions, previous surgeries that were performed, genetic conditions and such. For example, the system may ask about the patient's history, regarding his physical condition and his mental condition. For example, the system may ask if the patient has a history of high blood pressure, heart problems, fainting fits, dizziness, hypertension, strokes, diabetes, rheumatic fever, angina or hyperlipidemia. In addition, the system may ask if the patient has had any surgeries in the past. For example, the system may ask if the patient has had any cardiac procedures, or any other procedures. The system may ask questions regarding the patient's family history with respect to medical and genetic conditions. For example, the system may ask if the patient's family history includes hypertension, ischemic heart disease, strokes, diabetes, hyperlipidemia, or congenital heart disease. The system may also ask questions regarding the patient's lifestyle. For example, the system may ask if the patient smokes. In addition, the system may ask if the patient generally maintains a healthy or unhealthy diet and whether the patient exercises regularly.

The system may also ask questions regarding the patient's physical exam. For example, the system may ask questions regarding his vitals, general physical information, his neck, his respiratory system, his cardio vascular system, his abdomen, his genitourinary system, his skin and his extremities. For example, the system may ask if the patient is experiencing any chest pain or discomfort. If the patient answers that he is experiencing chest pain, the system may follow up with asking the patient to identify the location of the chest pain (i.e. in the front of the chest, the upper abdomen, the neck, the jaw, the left arm, or the left shoulder.) Similarly, the system may ask if the patient is experiencing shortness of breath, palpitations.

The system may also ask questions regarding his eyes. For example, the system may ask questions regarding his visual acuity, motility, visual fields, color testing, stereopsis, topography, anterior segment, tonometry, and opthalmoscopy.

The system may also ask questions regarding the patient's neurological system. For example, the system may ask questions regarding his mental status, his cranial nerves and his motor skills and his sensory skills After the medical history information is entered, the process proceeds to 450 to allow the user to upload images to the system. The system allows the user to upload any documents from any imaging tests such as X-Rays, Cat Scans, MRI, MRA, Ultra Sound and other scans.

The system also allows the user to upload any documents he received from any hospitalization visits he endured. In addition, the system allows the user to upload documents relating to diagnostic tests such as: Cardiac Catheterization, Carotid & Extremity Vascular testing, Cardiac Mapping, Echocardiography, Electrophysiology Study, Exercise Stress Tests, Holter & Event Loop Monitoring, Nuclear Cardiology Tests, Thyroid Scan, Bone Density Test, Endoscopy, Colonoscopy, EEG, EMG, and Nerve Conduction Studies. Any medical image files that the patient has may be uploaded to the system during this step. After the user uploads the images, the process for initiating the generation of a second medical opinion is complete.

The flow chart has both a start 405 and an end 495, but the process is cyclical in nature.

Turning now to FIG. 5, there is shown a flowchart for the process 500 of generating an objective second medical opinion. The process 500 starts after the patient has logged in securely into the system, and the HIPAA compliance is verified.

At 510, the system presents a list of symptom categories to the patient. The patient likely will view the system categories on a display, such as display 216 of FIG. 2. The user will review the categories, and then at 515, the user will select the category that fits his medical concern. Examples of categories that might be presented are "Pain in Back", "Pain in Chest."

After the user selects a category, then at 520, the system stores the category information that was selected in a database located in the storage, such as storage 224 in FIG. 2. After the system stores the category information in a database, the system provides the user the opportunity to select another category at 525. If another category is selected, then the process proceeds to 515 allowing the user to select another category. The categories may be identified by uniquely-identifiable numbers in a database such that a cross-section of several numbers may be associated with one or more medical conditions. This process may enable the system and the physician responsible for the second opinion report to more easily identify symptoms associated with particular medical conditions.

If the user does not select another category at 525, then the process proceeds to 530 where the system begins generating questions based on the category that was selected. For example, if the system determined that the user's medical concern related to "Gastroentology", the system might ask the user if he is having trouble swallowing or if he is experiencing abdominal pain. Based on the user's answer to the first question, the system will generate another question at 535. For example if the user answers affirmatively that he is having trouble swallowing, the system may ask if he is feeling any obstruction in his throat, or if he is experiencing a burning sensation after eating, or if he is feeling bloated. Similarly, if the user answers affirmatively that he is experiencing abdominal pain, the system may ask what type of pain he might be experiencing, such as burning pain or colic pain. The system may also ask whether the pain is in the user's left upper quadrant, or in his right upper quadrant. The system may also ask if the user is feeling any indigestion. Based on the user's answers, the system may ask about the user's After the user answers the questions that are generated by the system, the system begins identifying potential symptoms at 540. If the system is unable to identify potential symptoms based on the answers received, then the process proceeds back to 535 to generate additional questions for the user to answer.

After the system is able to identify potential symptoms, the system stores potential symptoms in a patient profile at 545. The process then proceeds to 550 to determine whether the process of answering all questions relating to a category is completed. If the user selected multiple categories of symptoms, then the system needs to generate questions and receive answers for each category that the user selected. If the process has not been completed for all the categories, then the process proceeds back to step 530 in which the system generates additional questions based on the categories that remain to inquire about. If the process has completed for all of the categories, then the process proceeds to step 555 wherein the system compiles all of the potential symptoms.

At 560, the system identifies potential conditions based on all of the questions and answers received. For example, if the user said initially that he had pain in his chest and he had difficulty breathing, the system may conclude that the user may have bronchitis. At 465, the system stores the potential condition in the patient profile.

Turning now to FIG. 6, a process 600 for initiating the generation of a second medical opinion is seen from a physician's perspective. Physicians may apply to be a part of the consulting panel for advising the patient on the medical second opinion. The system provides a web interface for physicians to review a summary of the patient's medical information, the symptoms, health information, test results and diagnostic images in high resolution.

Step 610 requires the physician to connect to the Internet via a secure connection, such as SSL or S-HTTP. The physician initiates a session by entering a URL which will allow the physician to connect to the system. After the physician initiates the session, the physician needs to first login into the system at 615. The physician likely has already registered with the system, which probably happened when the physician agreed to participate in the system. Therefore, the physician can login into the system using the login information he probably already has.

After the physician logs in, the system verifies the physician's login credentials. After the physician has logged in, the system establishes a secure connection, at 620, between the physician's system and the second opinion expert system, such as physician system 230 and second opinion expert system 220 in FIG. 2.

After a secure connection is established, a HIPAA security check is performed and a HIPAA transaction log is created. As required by the HIPAA privacy and security rules, the transaction log created will conform to the HIPAA standards.

Following the HIPAA checks, the system determines whether the physician has pending second opinion requests at 625. For example, the physician may have multiple suggested reports that the physician needs to review and finalize with his comments. If that is the case, then the physician begins the second opinion report review process at 635. At 640, the system determines whether the second opinion request is complete. If the second opinion request is not complete, then the process proceeds to 645, where the physician reviews the request and the system performs a data validation check.

If the second opinion request is complete, then the process proceeds to 650 to determine if the second opinion request is valid for a physician. If the request is not valid for a physician, then the second opinion request is sent back to be re-assigned to another physician at 660.

If the second opinion request is valid for a physician, then the user is notified of the finalized report at 670.

FIGS. 7, 8 and 9 show processes for uploading medical records and transmitting medical records into the system. The processes allow a user to upload a medical record and the system then associates the medical record with that particular patient. The system allows the user to upload multiple medical records into the system.

FIG. 7 shows the process 700 for uploading a digital medical record. At 710, the system determines whether the user has multiple records in the database. A user may have multiple records in a database if he has opened multiple cases in the system. If the user has multiple records, then at 715, the user has to select which record this medical record belongs to.

Once the accurate medical record has been selected, the user selects the digital upload method at 720. The user can also identify whether he wishes the document to be scanned at 725 and whether there is a photo in the document at 730. Once the user selects the options for the upload, then the user may upload the document at 735.

After the upload is complete, the digital images are stored in a database at 740, for 226 in FIG. 2. After the upload is complete, then the patient record is updated in the database to identify that documents exist for that record.

FIG. 8 shows the process 800 for faxing a medical record. At 810, the user faxes a medical document to a phone number connected to the system. At 820, the system converts the faxed document data to digital data. At 830, the system reviews the records in the database and determines whether the user for whom the document pertains is in the system. If the user is in the system, then the process proceeds to 840 to see if there is a record match.

If there is not a record match in the database, then the process proceeds to 870 to validate the data and determine to whom this document belongs.

If there is a record match in the database, then the digital copy of the faxed document is stored in the database at 850. At 860, the user's record is updated in the database to reflect that a medical document is saved for that user.

FIG. 9 shows the process 900 for uploading documents to the Dicom database. At 910, the system determines whether the user has only one record or if the user has multiple records. At 915, if the user has multiple cases, then the user is asked which case he is working on.

After he selects the case that the image is to be applied to, he selects that he wants to upload a Dicom image. At 925, the user uploads the Dicom image and the system receives the image. At 930, the user may also upload the Dicom image. At 935, the user may also choose to use a secure FTP connection to upload the Dicom image.

At 940, the system imports the Dicom images and the images are stored in 945.

At 950, the Dicom image in the database is updated to reflect that it is a document for the user. At 955, the user's record in the database is updated to reflect that he has uploaded a Dicom image for his case.

Figure 10:
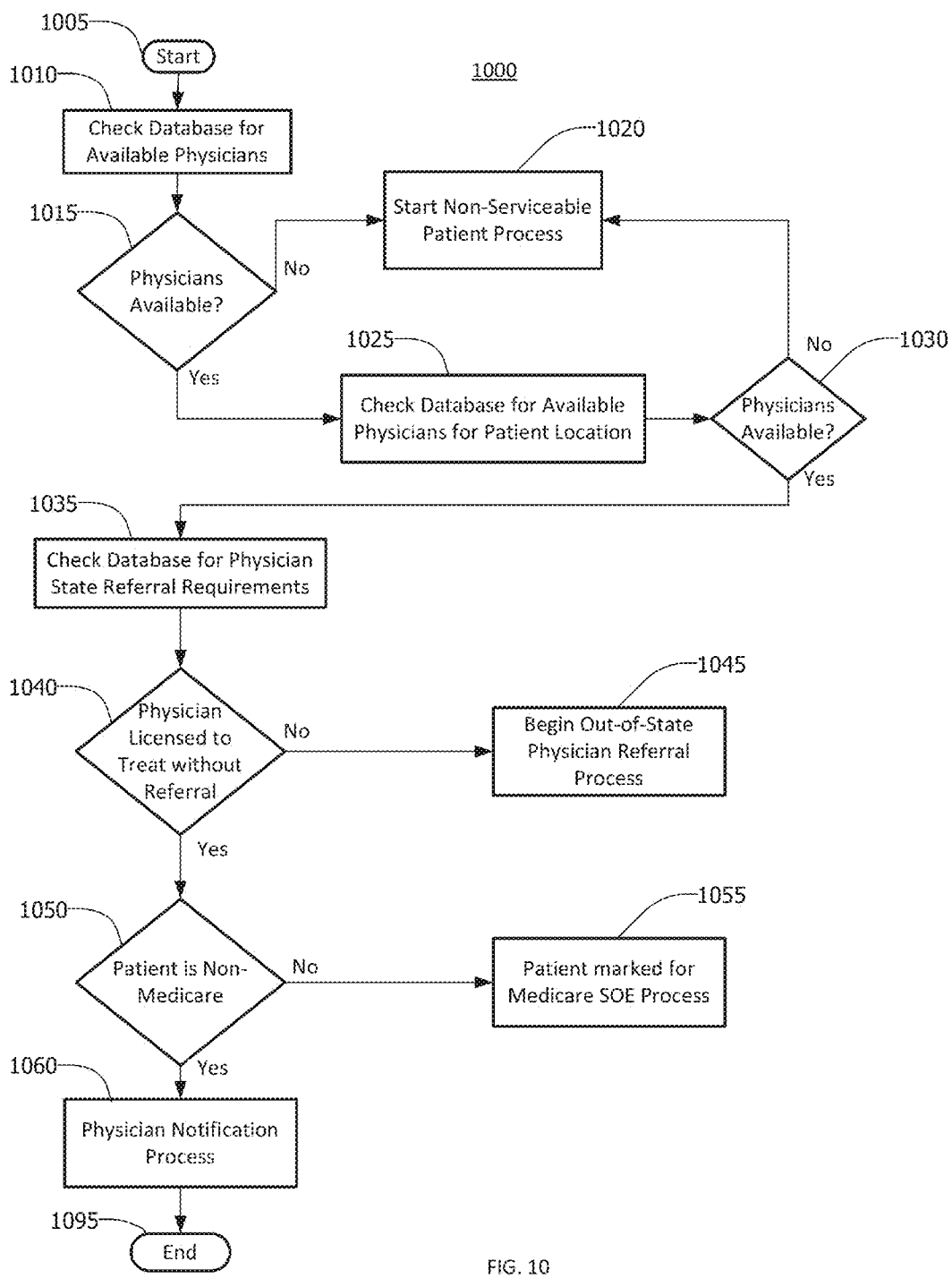
FIG. 10 is a flowchart for identifying a physician to review the second medical opinion report.

Turning now to FIG. 10, there is shown a flowchart 1000 for identifying a physician to review the second medical opinion report. At 1010, the system checks for available physicians in the database. At 1015, it determines if there are any physicians available. If there are, then the system checks whether there are any physicians available at the patient's location at 1025. If there aren't any physicians available for the chosen specialty, then the process proceeds to 1020 where the system starts a non-serviceable request. If there aren't any physicians available near the patient's location, then the process proceeds to 1020 where the system starts a non-serviceable request.

If there is a physician available at 1030, then the system checks the physician's state referral requirements at 1035. The system then checks if the physician is licensed to treat without a referral at 1040 and if the patient is a non-Medicare patient at 1050. If the physician is not licensed to treat without a referral, then the system begins an out-of-state physician referral process at 1045.

If the patient is a Medicare patient, then at 1055, the patient is marked for a Medicare second opinion report. If the patient is not a Medicare patient, then at 1060, a physician is notified that a second opinion expert case is ready for him.

Turning now to FIG. 11, this figure shows a process for an evidence based diagnosis. This process occurs after the user has completed the process shown in FIG. 5. At 1110, the system generates questions for the user to answer relating to the user's medical condition. As in FIG. 5, the user will identify a category of symptom that addresses his medical concern and the system will generate questions based on the category the user selected.

The system determines whether the process of generating questions is over. This is determined based on whether the system was able to determine a potential medical condition. If the process of generating questions is not complete, then the system notifies the user that the questionnaire relating to his symptoms is incomplete. The system then shows the user the questions that have already been asked and answered. The user then continues the process to complete the questions generated by the symptom to aid the symptom in identifying a potential condition.

After the process of completing the questionnaire is completed, the process proceeds to 1115 where the system orders the answers in a hierarchy based on the relevance. For example, if the patient stated that he had pain in his chest, and answered questions relating to his breathing and answered question suggesting hair loss, the system may group the answers relating to his breathing as more relevant than the answers relating to any possible hair loss.

After the system orders the answers received in a hierarchy based on relevance, the system formulates a clear clinical question based on the patient's symptom at 1125. An example of a clinical question might be, "Could the patient have bronchitis?"

After the system generates a clinical question, the system reviews whether the patient submitted any test data. For example, the system may determine whether the patient uploaded any images showing an X-Ray of the patient's lungs. Alternatively, if the patient was experiencing heart problems, the patient may have stress test results that he has uploaded to the system.

If the patient has uploaded test data, then, at 1130, the system extracts the key result data from the test results that were uploaded. For example, if a stress test was performed on the user's heart, then maybe only certain data might be extracted from the stress test.

After the data from the tests have been extracted, then at 1135, the system aggregates various information, including the patient's medical history, results from the medical tests, and treatment outcomes. The system then performs an evidence based analysis, at 1140, to determine a potential diagnosis based on the patient history, the key result data and the answers received from the user when the system generated questions based on the categories selected. The evidence based diagnosis includes reviewing all the various pieces of information and based on the results, or evidence, assessing a possible condition.

After the system performs the evidence based diagnosis, the system confirms whether the system was able to determine a diagnosis at 1145. If the system has determined a diagnosis, then the system generates a suggested second opinion at 1160, which is discussed in FIG. 12. If the system has not determined a diagnosis, the system will store the user input conditions in the database in the system at 1150. After the system has stored the information relating to the user's conditions, the system will then generate a suggested second opinion at 1155, as shown in FIG. 12. After the system has generated a suggested second opinion report, the system will obtain the physician's diagnosis at 1165. The physician will review the report and make changes or suggestions as required. After the physician has completed his diagnosis, then the system will update the evidence based diagnosis in the database at 1170.

Turning now to FIG. 12, a process for generating a suggested second opinion expert report is shown. The process begins by retrieving the patient's information from the database at 1210. The patient's information may include the patient's age and gender.

After that, the system retrieves the patient's history from the database at 1220. The patient's history may include the patient's medical history, the patient's physical history, the patient's family history, the patient's surgical history, and the patient's personal history. After retrieving the patient's medical history, the system retrieves the patient's symptom information from the database at 1230. This includes information relating to the patient's symptoms that he was experiencing. After retrieving the patient's symptom information, the system retrieves information relating to any digital or paper medical records that were uploaded at 1240 or Dicom image data that was uploaded at 1250.

After all of these categories of information are retrieved, the system then requests a potential diagnosis at 1260. The system analyzes all of the information that was gathered, and evaluates a potential diagnosis based on all of the information provided.

After the system determines a potential diagnosis, the system then generates a suggested second medical opinion report at 1270. The suggested second medical opinion report will be an extensive report listing in detail the patient's medical history, the questions generated by the system and the answers received in response to the questions relating to the patient's symptoms, the data that was extracted from any medical test results or diagnostic images. The report will also include links to the digital medical records, so that an individual reviewing the report will have a complete understanding of the patient's case up to that point.

Figure 13:
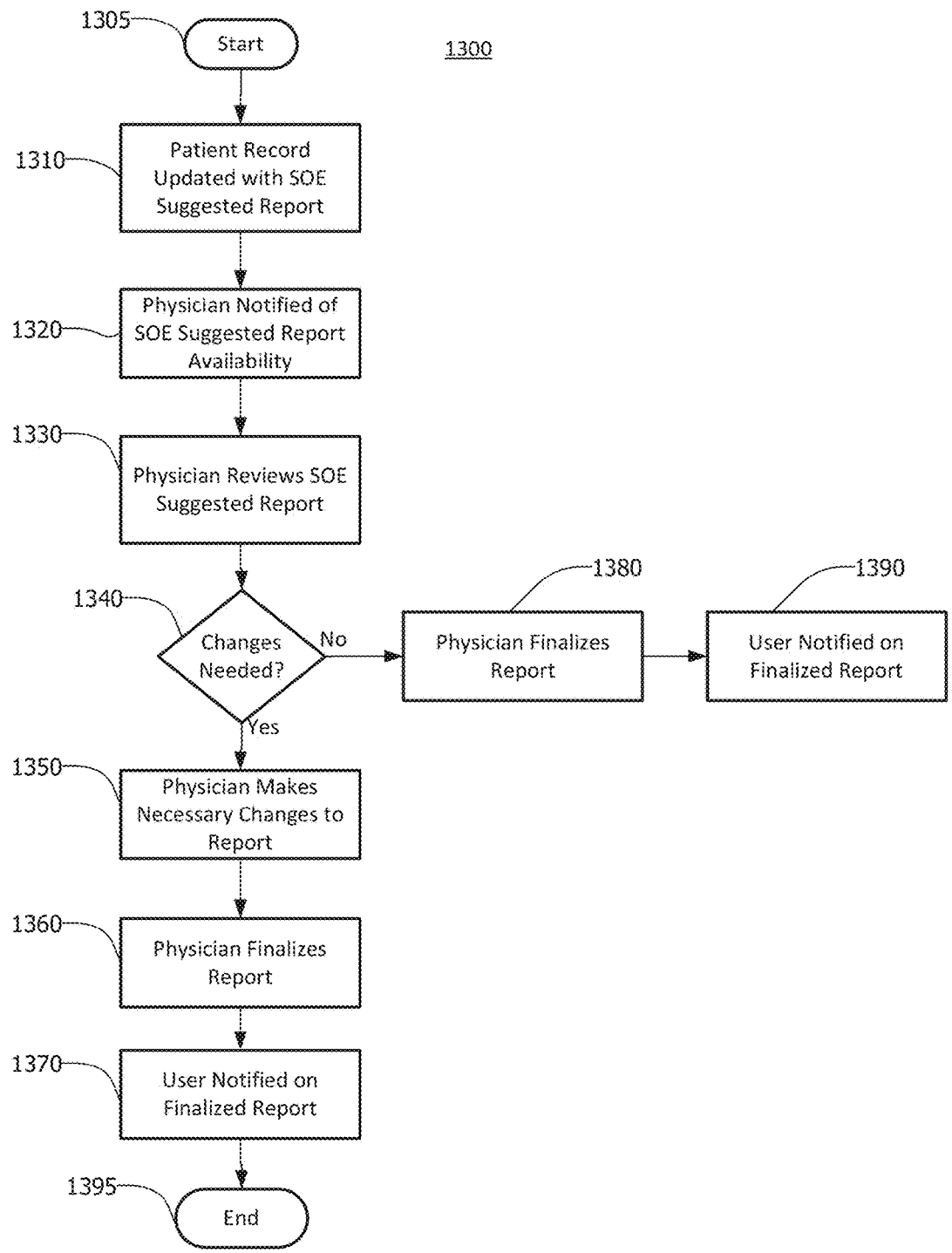
FIG. 13 is a flowchart for generating a final second opinion report.

Turning now to FIG. 13, there is shown a process 1300 for generating a final second opinion report. The process begins at 1310, by checking the system's database to determine if a patient's record has been updated with the suggested second opinion report which is prepared following the process discussed in FIG. 12. If the patient's record includes a suggested second medical opinion report, then the physician is notified that the report is available at 1320. The physician who is notified is the physician who was selected following the process shown in FIG. 10. After the physician is informed that the suggested second medical opinion exists in the database, the physician then reviews the suggested second medical opinion report at 1330.

The physician reviews the report and determines if any changes are needed at 1340. For example, the physician may determine that the diagnosis suggested in the report is not applicable based on answers the patient provided earlier to the system.

If no changes are needed, the physician finalizes the report at 1380. After the physician finalizes the report, the user is notified that the report has been finalized at 1390. The finalized report is sent to the system and the system stores the finalized report. The finalized report is also emailed to the user.

If changes are needed to the report, the physician makes all the necessary changes to the report at 1350. After the changes are completed, the physician finalizes the report at 1360 and the user is notified that the report is completed. The system stores the finalized report at 1370.

Figure 14:
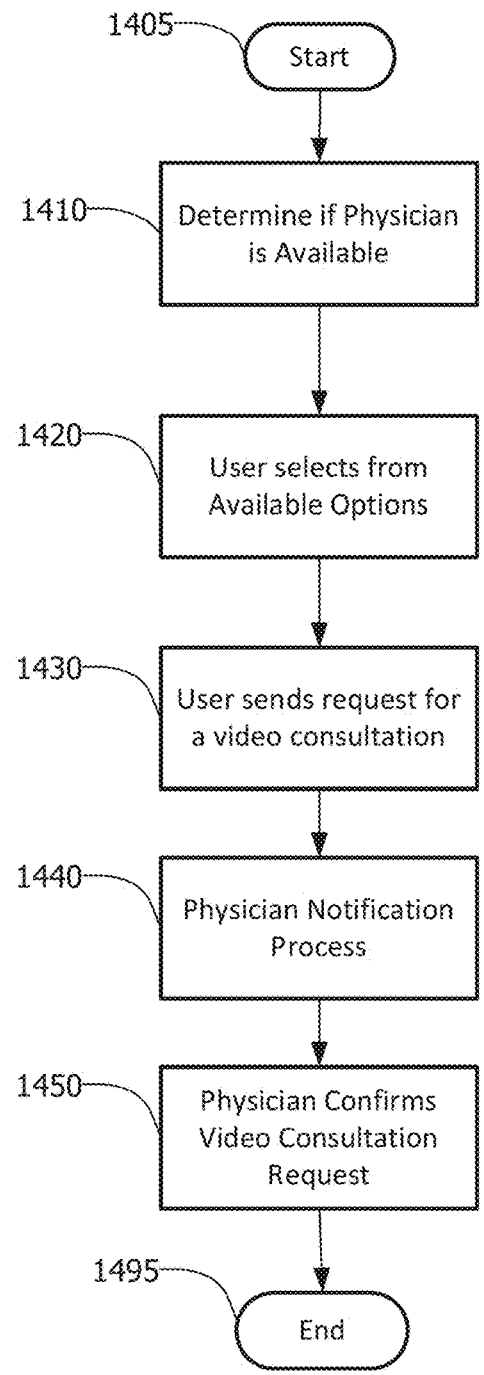
FIG. 14 is a flowchart for initiating a video consultation to review the second opinion report.

After the report has been finalized, the user has the option of initiating a request for a video consultation with the physician who finalized the report as seen in FIG. 14. The process for initiating a video consultation begins by checking the system for the physician's availability at 1410. When a physician registers with the system, the physician may provide days and times that he is available to consult with patients. This information may be stored in a database in the storage, such as storage 224 in FIG. 2.

The system then provides the user with a list of options to consult with the physician. The user selects one of the available options at 1420. The user then sends a request to have a video consultation with the physician at 1430. The physician is notified that the user would like to have a video consultation at 1440. The physician accepts the user's request to have a video consultation at 1450, and the video consultation is then scheduled between the user and the physician. The user then has the opportunity to ask any questions he has about the diagnosis or treatment recommended, or any other questions he may have regarding the report. In addition, the physician has an opportunity to ask any additional questions he may have that have not already been answered during the user dialogue with the system.

Figure 15:
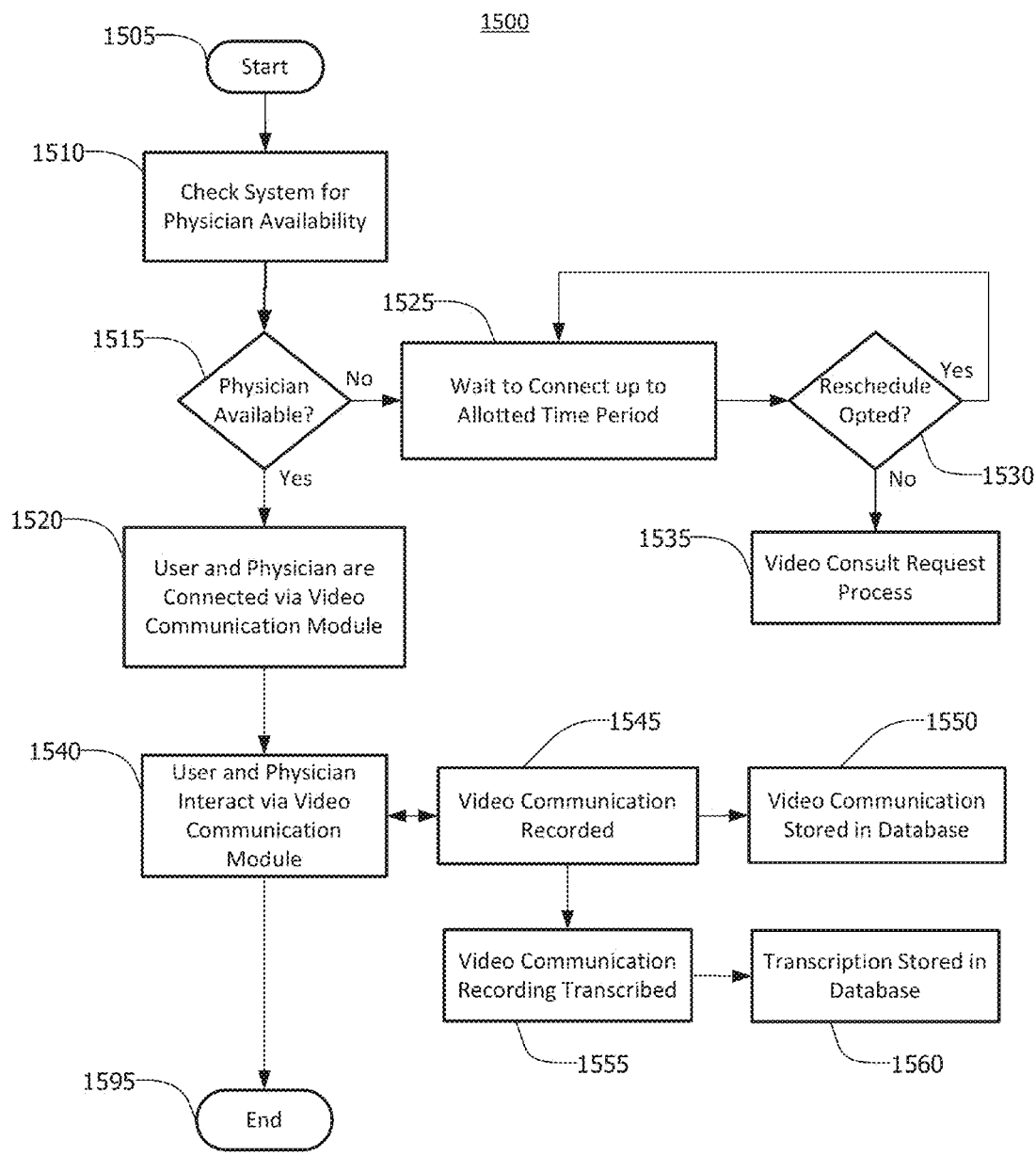
FIG. 15 is a flowchart for activating the video consultation to review the second opinion report.

After the video consultation has been scheduled, the process 1500 for activating the video conference begins as seen in FIG. 15. The first step in the process is for the user to initiate the video link. The user would need a webcam or similar device that has a camera to allow the physician to see the user. Similarly, the physician also would need to have a webcam or similar device to see the user.

After the user has initiated the video link, the system checks whether the physician is available at 1510. If the physician is available at 1515, the user and physician are connected via a video communication module and they can interact and the user can ask any questions he may have regarding the report at 1520. In addition, the physician may ask any questions he might have.

If the physician is not available, then the system waits until the scheduled time to connect the user to the physician at 1525. If the user wishes, he can choose to reschedule the video consultation if the physician is not available at 1530. If the user wishes to reschedule, then the system waits until the rescheduled time to attempt the video consultation at 1525. If the user does not wish to reschedule, then the system attempts to connect the user and the physician for the video consultation at 1535.

If the physician and user have a video consultation at 1540, the video communication will be recorded at 1545. The video communication will be stored in a database under the patient's profile at 1550. In addition, the video consultation will be transcribed at 1555 and the transcription will be stored in a database under the patient's profile at 1560. The patient then has an opportunity to login into the system at any time after the video consultation and review the transcribed notes, or the video communication regarding the consultation.

Figure 16:
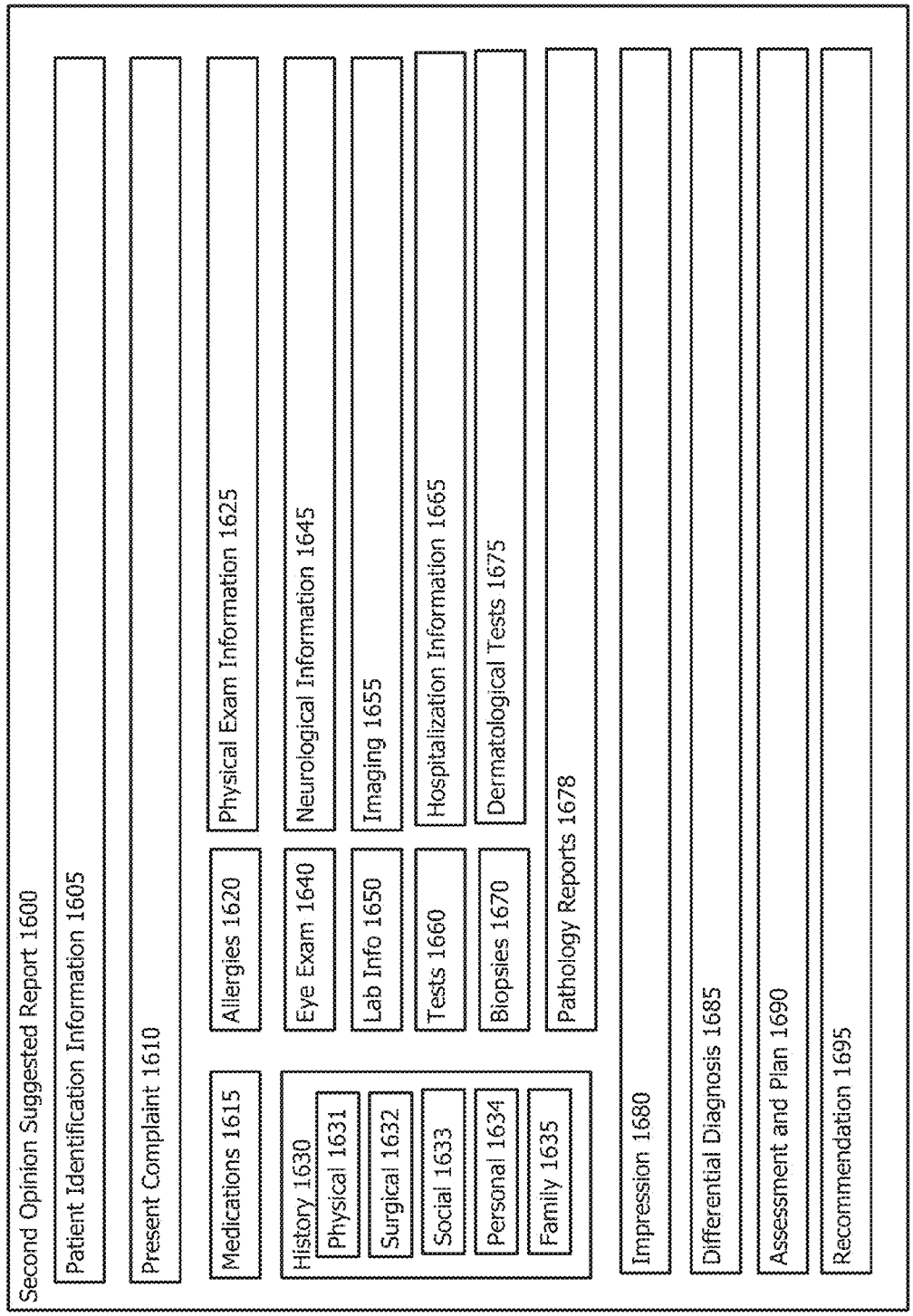
FIG. 16 is an example of a suggested second medical opinion report.

FIG. 16 is an example of a suggested second opinion report. The report can have various formats, and this is shown just as an example. The report 1600 has patient identification information 1605. This will include information regarding the patient's name, gender and age.

The report 1600 also includes the present complaint 1610. This can be a summary of the user's medical concern. Alternatively, it can be a hyperlink to the user's first medical opinion report that he received.

The report 1600 may also include information regarding the medications 1615 that the user is taking, including both prescription and non-prescription medications. The report 1600 may also include information regarding the user's allergies 1620. For example, this may include information regarding whether the patient is allergic to any medication or if the user is allergic to any environmental or food items.

The report 1600 may also include physical exam information 1625. This may include information regarding his vitals, general physical information, his neck, his respiratory system, his cardio vascular system, his abdomen, his genitourinary system, his skin and his extremities.

The report 1600 may also include historical information 1630. Specifically, the report may include physical information 1631, surgical information 1632, social information 1633, personal information 1634, and family information 1635. In addition, the report may include eye exam information 1640, neurological information 1645, and hospitalization information 1665. The report may also include lab information 1650, imaging information 1655, tests 1660, biopsies 1670, dermatological tests 1675 and pathology reports 1678, all of which may be hyperlinks to documents containing test data.

The report 1600 may also include an impression 1680 with a summary of what the medical concern might be. The report 1600 may also include a differential diagnosis 1685 which is the evidence based differential diagnosis that is generated after reviewing all of the patient's information. In addition, the report 1600 may also include an assessment and plan 1690 and a recommendation 1695. The assessment and plan 1690 and the recommendation 1695 are generated by the system as part of the suggested second opinion report and these provide the user with a plan and recommendation as to how to address his medical concern.

FIG. 16 is just included to provide as an example. The report may take many different forms and does not need to include all of the shown elements.

Closing Comments

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the methods described herein. Acts, elements and features discussed only in connection with one embodiment are not intended to be excluded from a similar role in other embodiments.

As used herein, "plurality" means two or more. As used herein, a "set" of items may include one or more of such items. As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, "and/or" means that the listed items are alternatives, but the alternatives also include any combination of the listed items.

Within this description, the term "engine" means a collection of hardware, which may be augmented by firmware and/or software that performs the described functions. An engine may typically be designed using a hardware description language (HDL) that defines the engine primarily in functional terms. The HDL design may be verified using an HDL simulation tool. The verified HDL design may then be converted into a gate netlist or other physical description of the engine in a process commonly termed "synthesis". The synthesis may be performed automatically using a synthesis tool. The gate netlist or other physical description may be further converted into programming code for implementing the engine in a programmable device such as a field programmable gate array (FPGA), a programmable logic device (PLD), or a programmable logic arrays (PLA). The gate netlist or other physical description may be converted into process instructions and masks for fabricating the engine within an application specific integrated circuit (ASIC).

Within this description, the term "unit" also means a collection of hardware, firmware, and/or software, which may be on a larger scale than an "engine". For example, a unit may contain multiple engines, some of which may perform similar functions in parallel. The terms "engine" and "unit" do not imply any physical separation or demarcation. All or portions of one or more units and/or engines may be collocated on a common card, or within a common FPGA, ASIC, or other circuit device.

Although shown implemented in a personal computer, the processes and apparatus may be implemented with any computing device. A computing device as used herein refers to any device with a processor, memory and a storage device that may execute instructions including, but not limited to, personal computers, server computers, computing tablets, set top boxes, video game systems, personal video recorders, telephones, personal digital assistants (PDAs), portable computers, and laptop computers. These computing devices may run an operating system, including, for example, variations of the Linux, Microsoft Windows, Symbian, and Apple Mac operating systems.

The techniques may be implemented with machine readable storage media in a storage device included with or otherwise coupled or attached to a computing device. That is, the software may be stored in electronic, machine readable media. These storage media include, for example, magnetic media such as hard disks, optical media such as compact disks (CD-ROM and CD-RW) and digital versatile disks (DVD and DVD±RW); flash memory cards; and other storage media. As used herein, a storage device is a device that allows for reading and/or writing to a storage medium. Storage devices include hard disk drives, DVD drives, flash memory devices, and others.

It is claimed:

1. A method for generating an objective medical second opinion report comprising:
    a patient interacting directly with a computing device to identify a category of symptoms affecting the patient;
    the computing device generating a set of questions based on the category selected and a database including the patient's present and past health conditions, wherein the question is selected from a database that stores the category using a code to identify the category;
    the computing device receiving a set of answers directly from the patient to the set of questions presented from the patient interacting with the computing device;
    the computing device ordering the set of answers in a hierarchical manner based on a relevance of the set of answers to the category of symptoms;
    the computing device generating a clinical question based on the ordering of the set of answers, wherein the clinical question is selected from a database including a set of medical conditions;
    the computing device receiving a document directly from the patient, the document comprising data regarding the patient's first medical opinion received from a first medical professional, the document including a first medical diagnosis, and patient diagnostic image data or diagnostic procedure data;

the computing device extracting the first medical diagnosis and the patient diagnostic image data from the document;

the computing device encrypting the document and storing the encrypted document in the database;

the computing device generating a current status report including the clinical question generated by the computing device, and a hyperlink to the document, wherein the current status report highlights the clinical question generated by the computing device;

the computing device generating a suggested second opinion report that comprises a second medical opinion suggested by the computing device that suggests a solution, identifying an additional medical exam to be performed by the patient, and prepared using data extracted from the document, the answer received, the clinical question, and the database including the set of medical conditions, wherein the suggested second opinion report is transmitted to a licensed physician who is interacting with a second computing device, wherein the licensed physician is a physician who is a specialist in the area suggested by the solution in the preliminary objective medical second opinion report.

2. The method of claim 1 wherein the steps of generating a question, by the computing device, and receiving an answer, directly from the patient, are repeated to provide a diagnosis of a possible condition of the patient.

3. The method of claim 1 further comprising generating a final second opinion report in response to input by the physician based on the physician's analysis of the suggested second opinion report, the patient's medical history and the physician's experience.

4. The method of claim 3 further comprising storing the final medical second opinion report in a database and transmitting the final medical second opinion to the patient.

5. The method of claim 4 further comprising providing the patient with a set of licensed physicians to consult with regarding the medical second opinion, and the patient selecting a licensed physician to consult with regarding the medical second opinion.

6. The method of claim 1 wherein the patient requests a video consultation with the physician.

7. The method of claim 6 wherein the physician accepts the patient's requests to have a video consultation with the physician.

8. A system for generating an objective medical second opinion report comprising a storage medium storing a program having instructions which when executed by a processor will cause the processor to:

identify, directly on a computing device, a category of symptoms affecting a patient;

generate a set of questions based on the category selected and a database including the patient's present and past health conditions;

receive a set of answers directly from the patient to the set of questions presented from the patient interacting with the computing device;

order the set of answers in a hierarchical manner based on a relevance of the set of answers to the category of symptoms;

generate a clinical question based on the ordering of the set of answers, wherein the clinical question is selected from a database including a set of medical conditions;

receive, from the computing device, a document comprising data regarding the patient's first medical opinion received from a first medical professional, the document including a first medical diagnosis, and patient diagnostic image data or diagnostic procedure data;

extract the first medical diagnosis and the patient diagnostic image data from the document;

encrypt the document and storing the encrypted document in the database;

generate a current status report including the clinical question generated by the computing device, and a hyperlink to the document, wherein the current status report highlights the clinical question generated by the computing device;

generate an objective suggested medical second opinion report that comprises a second medical opinion suggested by the computing device that suggests a solution, identifying an additional medical exam to be performed by the patient, and prepared using data extracted from the document, the answer received, the clinical question, and the database including the set of medical conditions, wherein the suggested medical second opinion report is transmitted to a licensed physician who is interacting with a second computing device, wherein the licensed physician is a physician who is a specialist in the area suggested by the solution in the preliminary objective medical second opinion report.

9. The system of claim 8 wherein the step of generating a question and receiving an answer are repeated until the system can prepare a diagnosis as to a possible condition of the patient.

10. The system of claim 8 further comprising generating a final medical second opinion report based on the physician's analysis of the preliminary objective medical second opinion report, the patient's medical history and the physician's experience.

11. The system of claim 10 further comprising storing the final medical second opinion report in a database and transmitting the final medical second opinion to the patient.

12. The system of claim 11 further comprising providing the patient with a set of licensed physicians to consult with regarding the medical second opinion, and the patient selecting a licensed physician to consult with regarding the medical second opinion.

13. The system of claim 12 wherein the patient requests a video consultation with the physician.

14. The system of claim 13 wherein the physician accepts the patient's requests to have a video consultation with the physician.

15. The system of claim 8 wherein the generating the question and receiving the answers occurs over a secured connection.

16. The system of claim 13 wherein the video consultation is recorded.

* * * * *